United States Patent
Wixey et al.

(10) Patent No.: US 12,426,974 B2
(45) Date of Patent: Sep. 30, 2025

(54) SYSTEMS TO APPLY PRELOAD TENSION FOR SURGICAL INSTRUMENTS AND RELATED METHODS

(71) Applicant: Intuitive Surgical Operations, Inc., Sunnyvale, CA (US)

(72) Inventors: Matthew Aaron Wixey, San Jose, CA (US); William Burbank, Sandy Hook, CT (US); Thomas Grosvenor Cooper, Menlo Park, CA (US); Patrick Flanagan, San Diego, CA (US); Nicholas H. Ragosta, Sunnyvale, CA (US); Donald Frank Wilson, Jr., Santa Clara, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 591 days.

(21) Appl. No.: 17/488,881

(22) Filed: Sep. 29, 2021

(65) Prior Publication Data
US 2022/0015849 A1    Jan. 20, 2022

Related U.S. Application Data

(63) Continuation of application No. 16/333,886, filed as application No. PCT/US2017/056506 on Oct. 13, 2017, now Pat. No. 11,160,625.
(Continued)

(51) Int. Cl.
*A61B 34/00* (2016.01)

(52) U.S. Cl.
CPC ........ *A61B 34/71* (2016.02); *A61B 2034/715* (2016.02)

(58) Field of Classification Search
CPC .................. A61B 34/71; A61B 2034/715
(Continued)

(56) References Cited

U.S. PATENT DOCUMENTS

| 5,086,401 A | 2/1992 | Glassman et al. |
| 5,279,309 A | 1/1994 | Taylor et al. |

(Continued)

FOREIGN PATENT DOCUMENTS

| CN | 1235423 A | 11/1999 |
| CN | 101631516 A | 1/2010 |

(Continued)

OTHER PUBLICATIONS

Extended European Search Report for Application No. EP17860651.3, mailed on May 15, 2020, 8 pages.
(Continued)

*Primary Examiner* — Michael J Lau
(74) *Attorney, Agent, or Firm* — Jones Robb, PLLC

(57) ABSTRACT

A surgical system includes a dynamic preload tension feature for a tensioning element that actuates a distal end component of a surgical instrument. The surgical instrument includes a chassis at a proximal end of the surgical instrument, drive components mounted in the chassis, a distal end component at a distal end of the surgical instrument, a flexible tensioning element coupled between a first of the drive components and the distal end component, and a dynamic preload tensioner mounted in the chassis and coupled to a second of the drive components. The flexible tensioning element extends along a path. The dynamic preload tensioner is configured to be driven by the second of the drive components to be moved relative to the chassis and is positioned to change the path of the flexible tensioning element as the dynamic preload tensioner moves relative to the chassis.

19 Claims, 16 Drawing Sheets

Related U.S. Application Data

(60) Provisional application No. 62/408,242, filed on Oct. 14, 2016.

(58) Field of Classification Search
USPC .......................................................... 606/1
See application file for complete search history.

(56) References Cited

U.S. PATENT DOCUMENTS

| | | | |
|---|---|---|---|
| 5,417,210 | A | 5/1995 | Funda et al. |
| 5,887,121 | A | 3/1999 | Funda et al. |
| 6,208,170 | B1 | 3/2001 | Iwaki et al. |
| 6,331,181 | B1 | 12/2001 | Tierney et al. |
| 7,837,674 | B2 | 11/2010 | Cooper |
| 8,277,443 | B2 | 10/2012 | Jinno |
| 8,828,023 | B2 | 9/2014 | Neff et al. |
| 9,295,524 | B2 | 3/2016 | Schena et al. |
| 11,160,625 | B2 * | 11/2021 | Wixey ............... A61B 34/71 |
| 2002/0032451 | A1 | 3/2002 | Tierney et al. |
| 2002/0087166 | A1 | 7/2002 | Brock et al. |
| 2004/0049205 | A1 * | 3/2004 | Lee .................. A61B 34/37 606/130 |
| 2007/0142969 | A1 * | 6/2007 | Devengenzo ......... A61B 34/71 700/245 |
| 2010/0082041 | A1 | 4/2010 | Prisco |
| 2011/0313405 | A1 * | 12/2011 | Anderson ........... A61B 34/71 606/1 |
| 2012/0046522 | A1 * | 2/2012 | Naito ................ A61B 1/0052 600/118 |
| 2012/0289974 | A1 | 11/2012 | Rogers et al. |
| 2013/0304084 | A1 * | 11/2013 | Beira ................ F16H 19/08 74/89.22 |
| 2014/0025046 | A1 | 1/2014 | Williams et al. |
| 2014/0107665 | A1 * | 4/2014 | Shellenberger ...... A61B 34/37 606/130 |
| 2014/0128849 | A1 * | 5/2014 | Au .................... A61B 34/30 606/1 |
| 2014/0276613 | A1 * | 9/2014 | Goodman ......... A61M 25/0147 604/95.04 |
| 2015/0012021 | A1 * | 1/2015 | Mihara ............... A61B 1/018 606/1 |
| 2015/0038981 | A1 | 2/2015 | Kilroy et al. |
| 2015/0238267 | A1 | 8/2015 | Devengenzo et al. |
| 2016/0030120 | A1 * | 2/2016 | Yanagihara ......... A61B 1/0055 606/130 |
| 2016/0113732 | A1 | 4/2016 | Steege et al. |
| 2016/0128792 | A1 | 5/2016 | Rogers et al. |
| 2016/0184036 | A1 * | 6/2016 | Solomon ............ B25J 9/1641 606/130 |
| 2016/0192927 | A1 * | 7/2016 | Kostrzewski ...... A61B 17/0643 227/176.1 |
| 2016/0193001 | A1 * | 7/2016 | Lee .................. A61B 34/71 606/130 |
| 2016/0287840 | A1 * | 10/2016 | Jiang ............... A61M 25/0147 |
| 2017/0014196 | A1 * | 1/2017 | Seow ................ F16H 19/08 |
| 2019/0307522 | A1 | 10/2019 | Lambrecht et al. |

FOREIGN PATENT DOCUMENTS

| | | |
|---|---|---|
| CN | 102770060 A | 11/2012 |
| CN | 103565487 A | 2/2014 |
| CN | 104582594 A | 4/2015 |
| CN | 105163679 A | 12/2015 |
| CN | 105473095 A | 4/2016 |
| CN | 105943095 A | 9/2016 |
| CN | 105979889 A | 9/2016 |
| EP | 3040045 A1 | 7/2016 |
| WO | WO-2014151952 A1 | 9/2014 |
| WO | WO-2015023840 A1 | 2/2015 |
| WO | WO-2015175200 A1 | 11/2015 |
| WO | WO-2016064616 A1 | 4/2016 |
| WO | WO-2016129336 A1 | 8/2016 |
| WO | WO-2016136301 A1 * | 9/2016 ......... A61B 1/00009 |

OTHER PUBLICATIONS

International Search Report and Written Opinion for Application No. PCT/US2017/056506, mailed on Jan. 19, 2018, 14 pages.
Office Action mailed Dec. 17, 2020 for Chinese Application No. 201780063196 filed Oct. 13, 2017, 31 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.
Office Action for Chinese Application No. CN202111664385.8, mailed Dec. 29, 2023, 23 pages.
Extended European Search Report for Application No. EP24220822.1 mailed on Mar. 27, 2025, 10 pages.

\* cited by examiner

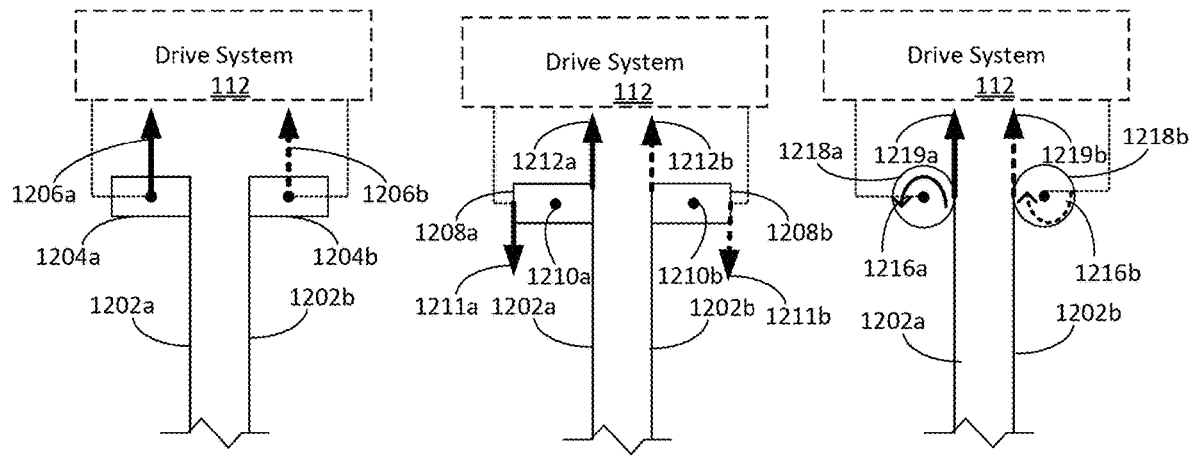
FIG. 12A     FIG. 12B     FIG. 12C
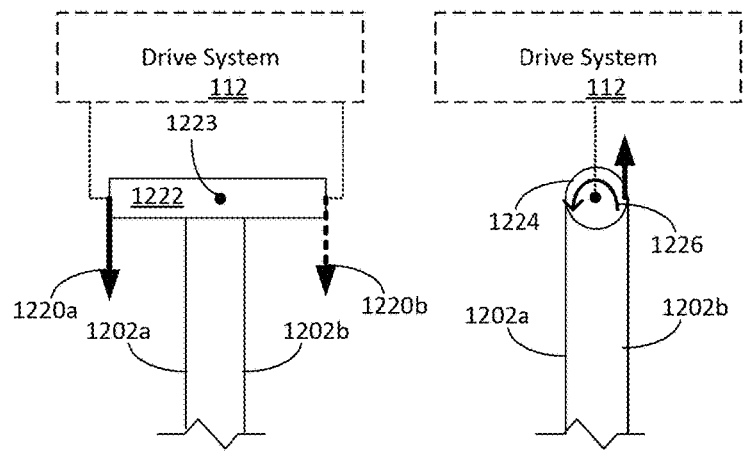
FIG. 12D     FIG. 12E

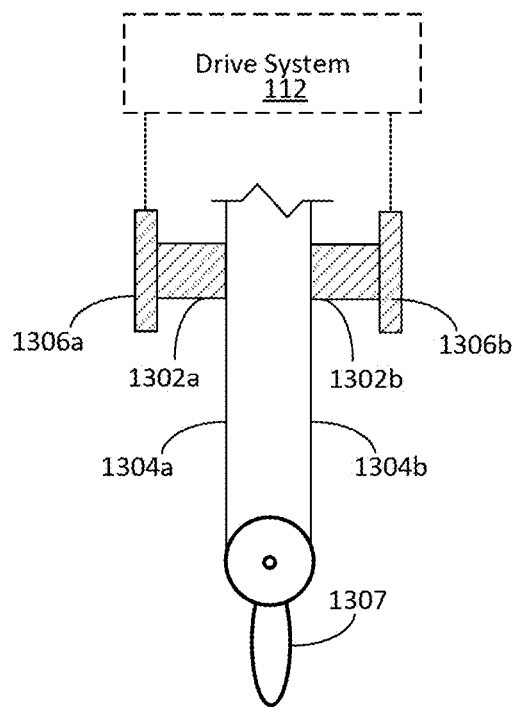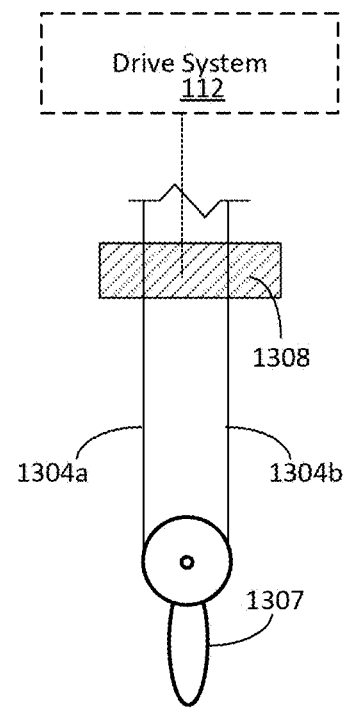
FIG. 13A  FIG. 13B

SYSTEMS TO APPLY PRELOAD TENSION FOR SURGICAL INSTRUMENTS AND RELATED METHODS

CROSS REFERENCE TO RELATED APPLICATIONS

This application is a continuation of and claims the benefit of priority to U.S. patent application Ser. No. 16/333,886, now U.S. Pat. No. 11,160,625, filed on Mar. 15, 2019, which is a U.S. National Stage Application under 35 USC § 371 and claims the benefit of International Patent Application No. PCT/US2017/056506 filed on Oct. 13, 2017, which claims the benefit of U.S. Provisional Application No. 62/408,242, filed Oct. 14, 2016. The disclosure of the prior applications are considered part of and are incorporated by reference in the disclosure of this application.

TECHNICAL FIELD

This specification relates to systems and methods to apply preload tension for surgical instruments, particularly for flexible tensioning elements for surgical instruments.

BACKGROUND

Slack or low tension in cables of a surgical instrument may in some situations cause jumpy or unpredictable motion of an end effector of the surgical instrument. One way to ensure that sufficient cable tension exists throughout a surgical instrument's design life is to preload the cable with sufficiently high tension to withstand some preloaded cable tension degradation, particularly when the end effector may be used for pushing and pulling, clamping, gripping, or other actions that encounter resistance. However, the tension preload in the cables can increase the forces that a drive system must apply to operate the surgical instrument. The preload can increase friction where the cables ride along surfaces of the surgical instrument. The preload can also cause friction where the cables contact curved surfaces of an opening through which the cables pass.

SUMMARY

In one aspect, a computer-assisted surgical system includes a surgical instrument. The surgical instrument includes a chassis at a proximal end of the surgical instrument, drive components mounted in the chassis, a distal end component at a distal end of the surgical instrument, a flexible tensioning element coupled between a first of the drive components and the distal end component, and a dynamic preload tensioner mounted in the chassis and coupled to a second of the drive components. The flexible tensioning element extends along a path. The dynamic preload tensioner is configured to be driven by the second of the drive components to be moved relative to the chassis and positioned to change the path of the flexible tensioning element as the dynamic preload tensioner moves relative to the chassis.

In another aspect, a method includes moving a dynamic preload tensioner of a surgical instrument to increase tension in a flexible tensioning element of the surgical instrument. The method further includes driving the flexible tensioning element of the surgical instrument to move a distal end component of the surgical instrument while a position of the dynamic preload tensioner is maintained.

In some implementations, the system includes a manipulator on which the surgical instrument is mounted. The manipulator includes, for example, a first drive output positioned to drive the first of the drive components of the surgical instrument and a second drive output positioned to drive the second of the drive components of the surgical instrument.

In some implementations, the system further includes a memory and a computer processor configured to execute instructions stored in the memory to perform operations. The operations include, for example, driving the second of the drive components to move the dynamic preload tensioner from a first position to a second position. The method includes, for example, moving the dynamic preload tensioner includes driving a first of drive components to move the dynamic preload tensioner from a first position to a second position. In some cases, the second of the drive components is driven when the processor receives information indicating the instrument is mounted to the manipulator. In some cases, the operations further include driving the second of the drive components until the processor receives information indicating that a predefined tension in the flexible tensioning element is reached. The method includes, for example, driving a second of the drive components after receiving information indicating that a predefined tension in the flexible tensioning element is reached. In some cases, the information indicative of the predefined tension in the flexible tensioning element is based on a torque of an actuator driving the second drive output.

In some implementations, the operations and/or the method include maintaining the position of the dynamic preload tensioner in response to determining that the tension in the flexible tensioning element has reached a predefined tension. The operations and/or the method include, for example, detecting the tension in the flexible tensioning element while moving the dynamic preload tensioner. Maintaining the position of the dynamic preload tensioner includes, for example, maintaining the position of the dynamic preload tensioner in response to the detected tension reaching the predefined tension. In some cases, moving the dynamic preload tensioner includes operating an actuator to cause the dynamic preload tensioner to move. Detecting the tension in the flexible tensioning element includes, for example, detecting a torque applied by the actuator.

In some implementations, moving the dynamic preload tensioner includes operating a second of multiple drive components of the surgical instrument. The method and/or the operations further include, for example, operating a first of the drive components to drive the flexible tensioning element to move a distal end component of the surgical instrument. In some cases, operating the first of the drive components to drive the flexible tensioning element includes operating the first of the drive components while maintaining the position of the dynamic preload tensioner.

In some implementations, moving the dynamic preload tensioner includes moving the dynamic preload tensioner from a first position in which a first tension exists in the flexible tensioning element to a second position in which a second tension exists in the flexible tensioning element. In some implementations, at a first position of the dynamic preload tensioner, a first tension exists in the flexible tensioning element. At a second position of the dynamic preload tensioner, for example, a second tension exists in the flexible tensioning element. The second tension is, for example, larger than the first tension. In some cases, the first tension is zero.

In some implementations, moving the dynamic preload tensioner includes moving the dynamic preload tensioner such that an adjustable preload is applied to the flexible tensioning element. In some implementations, the dynamic preload tensioner is positioned to cause an adjustable preload to be applied to the flexible tensioning element when then the dynamic preload tensioner is moved relative to the chassis.

In some implementations, moving the dynamic preload tensioner includes moving the dynamic preload tensioner to change a path of each of multiple flexible tensioning elements of the surgical instrument. In some implementations, the system includes multiple flexible tensioning element each coupled to the drive components mounted in the chassis. The dynamic preload tensioner is movable relative to the chassis, for example, to change a path of each of multiple flexible tensioning elements.

In some implementations, the flexible tensioning element is formed from a polymer material.

In some implementations, the dynamic preload tensioner includes a tensioning drum axially movable such that the tensioning drum engages the flexible tensioning element when the tensioning drum is rotated. In some implementations, moving the dynamic preload tensioner includes rotating a tensioning drum to cause the tensioning drum to move axially to engage the flexible tensioning element. In some cases, the dynamic preload tensioner includes a tensioning gear mounted to the chassis and rotatable along a ramp. In some cases, the ramp is defined by the chassis. In some cases, the tensioning drum is coupled to the tensioning gear such that the tensioning drum moves axially when the tensioning gear is rotated along the ramp of to the chassis of the surgical instrument. In some cases, the dynamic preload tensioner includes a spring engaged with the tensioning drum such that a static preload is applied to the flexible tensioning element. In some cases, the tensioning drum is movable to compress the spring such that coils of the spring contact one another when the path is changed.

In some implementations, the method and/or the operations include applying a static preload to the flexible tensioning element before moving the dynamic preload tensioner.

In some implementations, moving the dynamic preload tensioner includes compressing a spring such that coils of the spring contact one another when the tension in the flexible tensioning element reaches a predefined tension.

In some implementations, moving the dynamic preload tensioner includes rotating a lead screw of the surgical instrument to increase the tension in the flexible tensioning element. In some implementations, the dynamic preload tensioner includes a lead screw and an arm coupled to the lead screw. In some cases, rotating the lead screw includes moving an arm of the surgical instrument longitudinally to increase the tension in the flexible tensioning element. In some cases, the arm is movable longitudinally along the lead screw to change the path when the lead screw rotates.

In some implementations, moving the dynamic preload tensioner includes moving an elongate body of the surgical instrument relative to a chassis of the surgical instrument to increase the tension in the flexible tensioning element. In some implementations, the surgical instrument includes an elongate body extending distally from the chassis. A distal end of the elongate body is, for example, coupled to the distal end component. The elongate body contains, for example, at least a portion of the path of the flexible tensioning element. The dynamic preload tensioner is, for example, configured to move the elongate body relative to the chassis to change the path when the dynamic preload tensioner is moved relative to the chassis.

In some implementations, moving the dynamic preload tensioner includes rotating a cam to engage the flexible tensioning element to increase the tension in the flexible tensioning element. In some implementations, the dynamic preload tensioner includes a cam rotatable relative to the chassis. A surface of the cam is, for example, configured to engage the flexible tensioning element to change the path when the cam is rotated.

In some implementations, moving the dynamic preload tensioner includes moving the dynamic preload tensioner to one of multiple discrete positions to apply one of multiple discrete preloads to the flexible tensioning element. Maintaining the position of the dynamic preload tensioner includes, for example, locking the dynamic preload tensioner to one of the multiple discrete positions. In some implementations, the dynamic preload tensioner is lockable to one of multiple discrete positions to apply one of multiple discrete preloads to the flexible tensioning element.

In some implementations, moving the dynamic preload tensioner includes operating a drive output of a surgical manipulator to which the surgical instrument is mounted. In some implementations, the system further includes an instrument drive unit to releasably support the surgical instrument. The instrument drive unit includes, for example, a drive output operably connected to the dynamic preload tensioner such that the dynamic preload tensioner moves relative to the chassis when the drive output is activated. In some cases, operating the drive output includes twisting the flexible tensioning element. In some cases, the method and/or the operations further include receiving information indicating that the surgical instrument is mounted to the surgical manipulator. In some cases, the drive output is operable to engage the dynamic preload tensioner such that the flexible tensioning element is twisted to change the path of the flexible tensioning element.

In some implementations, moving the dynamic preload tensioner includes moving a pin mounted to a chassis of the surgical instrument. In some implementations, the dynamic preload tensioner includes a pin movably mounted to the chassis and engageable with the flexible tensioning element to change the path of the flexible tensioning element when the pin is moved relative to the chassis.

In some implementations, moving the dynamic preload tensioner includes pivoting a plate mounted to a chassis of the surgical instrument. In some implementations, the dynamic preload tensioner includes a tensioning plate pivotably mounted to the chassis to change the path when the tensioning plate is rotated relative to the chassis.

In some implementations, the system further includes a manually operable tensioning tool.

Advantages of the foregoing may include, but are not limited to, those described below and herein elsewhere. The flexible tensioning element, to enable load to be transferred from a first end to a second end, may require an initial load that renders the flexible tensioning element taut. When the flexible tensioning element is taut, it is able to transfer additional load from its first end to it second end. The path of the flexible tensioning element may be adjusted to apply a preload to the flexible tensioning element. The flexible tensioning element, with a preload, can transfer a greater proportion of an input load toward its distal end to drive the distal end component to which the flexible tensioning element is physically coupled. In this regard, rather than being used to pull the flexible tensioning element taut, the input load is used to steer the distal end component to which the flexible tensioning element is coupled.

The adjustable path of the flexible tensioning element may further improve adaptability of the surgical instrument as conditions of the surgical instrument change. In some cases, during manufacture of the surgical instrument, the flexible tensioning element is provided with an initial preload to inhibit movement of components of the surgical instrument relative to one another before use in a surgical operation. As time elapses between completion of the manufacturing of the surgical instrument and the operation of the surgical instrument during the surgical operation, the initial preload can decrease over time, e.g., due to instrument aging, creep, stress relaxation, relative movement between instrument components, and other mechanisms that can reduce the initial preload. The path of the flexible tensioning element can be adjusted such that the preload in the flexible tensioning element can be precisely controlled, e.g., maintaining the preload within a desired range, maintaining the preload above a predefined threshold, etc. The preload can be adjusted so as to inhibit excess friction between the flexible tensioning element and surfaces bearing against the flexible tensioning while inhibiting likelihood that the flexible tensioning element becomes slack during operation of the surgical instrument.

In addition, because the preload can be adjusted after the completion of manufacturing of the surgical instrument, the initial preload set during manufacturing can be less because the preload can be further adjusted, e.g., increased, after the manufacturing is complete. When the initial preload is less, the likelihood of material changes to the flexible tensioning element, e.g., due to creep or stress relaxation, may be lower.

The details of one or more implementations of the subject matter described in this specification are set forth in the accompanying drawings and the description below. Other potential features, aspects, and advantages will become apparent from the description, the drawings, and the claims.

BRIEF DESCRIPTION OF THE DRAWINGS

FIGS. 12A-12E are diagrams of drive components coupled to flexible tensioning elements.

FIGS. 13A and 13B are diagrams of dynamic tensioners and flexible tensioning elements.

Like reference numbers and designations in the various drawings indicate like elements.

DETAILED DESCRIPTION

A flexible tensioning element (e.g., a cable, a cable-hypotube combination, or the like) of a surgical instrument includes a preload tension that enables an input tension load to be transferred through the flexible tensioning element from a first end to a second end. The preload tension can also inhibit the flexible tensioning element from becoming slack when another flexible tensioning element is loaded such that the flexible tensioning element relaxes. The preload tension corresponds to, for example, a tension existing in the flexible tensioning element absent an input tension load to drive a distal end component coupled to the flexible tension element, a tension existing in the flexible tensioning element before the input tension load is applied to drive the distal end component, a tension existing in the flexible tensioning element to reduce slack in the flexible tensioning element, etc. The preload tension, as described herein, can be adjusted, e.g., after the manufacturing of the surgical instrument is complete, to improve operability and adaptability of the surgical instrument.

As described herein, an instrument tensioning element initially experiences a first preload tension, which may be zero or another value sufficient to maintain the instrument's mechanical integrity during shipment, storage, etc. Either before or during operation of the instrument, a controller increases the instrument tensioning element's first preload tension to a second preload tension larger than the first preload tension. During operation, the tensioning element will experience two forms of tension—the second preload tension and the actuation tension load used to drive an instrument distal end component to which the tensioning element is coupled. After operation, the instrument tensioning element's second preload tension is optionally reduced to a value less than the second preload tension, such as the first preload tension. The reduction in preload tension may be controlled by the controller, or it may otherwise be manually or mechanically controlled when an instrument is removed from its instrument carriage after operation. The cycle of dynamically increasing and decreasing the instrument tensioning element's preload tension may optionally be repeated during one or more subsequent instrument operations or uses. Thus the instrument tensioning element experiences a dynamic change in preload tension that is controlled at least in part by a controller, in addition to the actuation tension load changes that are applied to move or allow movement of the distal end component.

Figure 1:
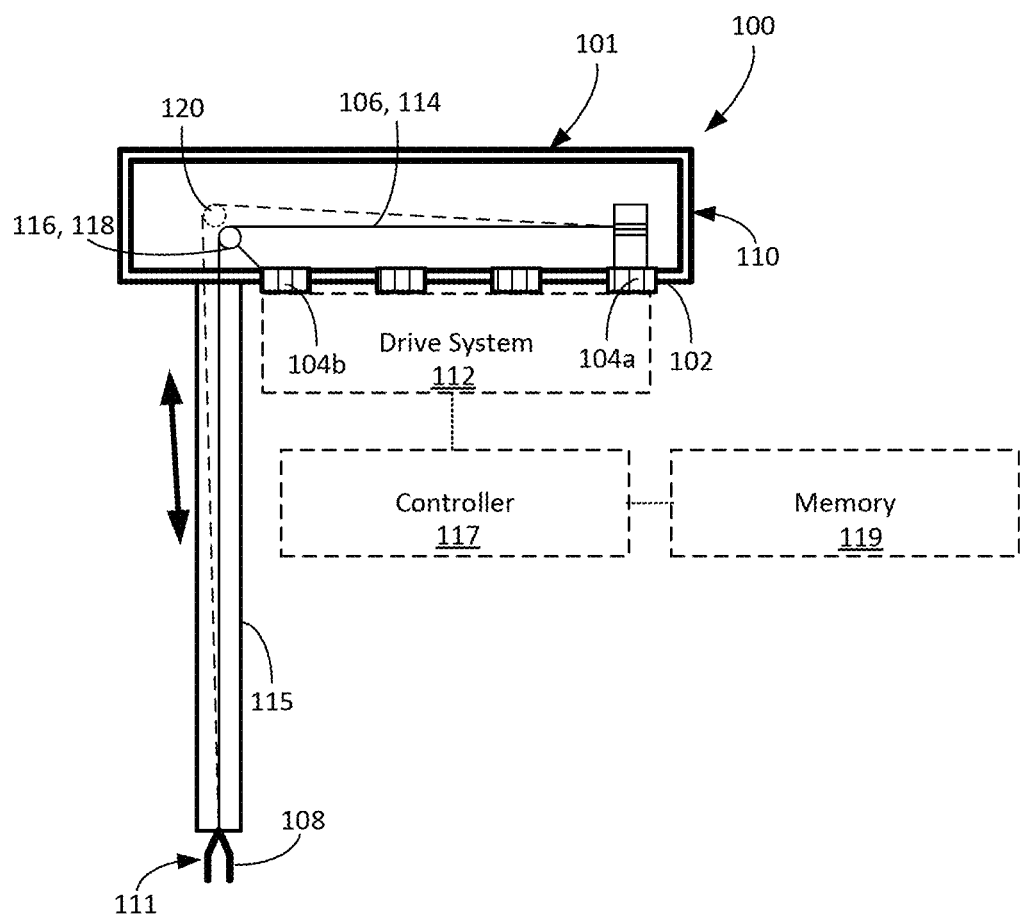
FIG. 1 is a schematic side view of a surgical instrument including a dynamic tensioner.

FIG. 1 depicts an example of a surgical system 100 including a surgical instrument 101 that includes a chassis 102, drive components 104a, 104b, a flexible tensioning element 106, and a distal end component 108. The drive component 104b is, for example, a dynamic preload tensioner drive component that is driven to manipulate a dynamic preload tensioner 116. The drive component 104a is, for example, a flexible tensioning element drive component that is driven to drive the flexible tensioning element 106. The chassis 102 is at a proximal portion 110 of the surgical instrument 101, and the distal end component 108 is at a distal portion 111 of the surgical instrument 101. The drive components 104a, 104b are mounted in the chassis 102, i.e., near or at the proximal portion 110 of the surgical instrument 101. The drive components 104a, 104b include, for example, mechanical components that carry mechanical load from a drive system 112. The drive components 104a, 104b are, for instance, driven components that move when driven by the drive system 112. The flexible tensioning element 106 is coupled between the drive component 104a and the distal end component 108. The flexible tensioning element 106 extends along a path, for example, between the drive component 104a and the distal end component 108. The drive component 104a transfers an actuation load applied to the drive component 104a to the flexible tensioning element 106.

The surgical instrument 101 further includes a dynamic preload tensioner 116. The dynamic preload tensioner 116 is, in some cases, mounted in the chassis 102. In some implementations, the dynamic preload tensioner 116 is at least partially mounted in the chassis 102 and/or entirely contained within the chassis 102. The dynamic preload tensioner 116 is coupled to the drive component 104b. The drive component 104a, in some cases, is coupled to a drive mechanism to transfer load applied to the drive component 104b to the flexible tensioning element 106. The dynamic preload tensioner 116 is configured to be driven by the drive component 104b to be moved relative to the chassis 102. In this regard, the dynamic preload tensioner 116 is controllably positioned to change the path of the flexible tensioning element 106 as the dynamic preload tensioner 116 moves relative to the chassis 102.

In some implementations, in cases in which the drive component 104a is driven, the drive component 104a applies an axial (e.g., lengthwise) actuation load to the flexible tensioning element 106. An axis of the axial load is, for example, parallel to an axis of a tension force in the flexible tensioning element 106. In cases in which the drive component 104b is driven, the drive component 104b operates the dynamic preload tensioner 116 to apply a transverse (e.g., crosswise) load to the flexible tensioning element 106. The transverse load, for instance, bends the flexible tensioning element 106 in a manner that induces a tension in the flexible tensioning element 106. In this regard, when the drive component 104b has not been driven to operate the dynamic preload tensioner 116, a first tension exists within the flexible tensioning element 106. The drive component 104b, when driven, causes a second tension to exist in the flexible tensioning element. The first tension corresponds to the preload tension in the flexible tensioning element 106 absent operation of the dynamic preload tensioner 116, and the second tension corresponds to a preload tension in the flexible tensioning element 106 after the drive component 104b has been operated. Due to the operation of the dynamic preload tensioner 116, the second tension is greater than the first tension.

While a single flexible tensioning element 106 is described and shown in FIG. 1, examples described herein are applicable to surgical instruments with a dynamic preload tensioner that simultaneously changes both the path of one flexible tensioning element and the path of another flexible tensioning element. Two flexible tensioning elements are, for example, coupled to the same drive component, e.g., the drive component 104a, or the flexible tensioning elements are coupled to independently operable drive components.

FIGS. 12A to 12E depict various examples of configurations of drive components to drive flexible tensioning elements 1202a, 1202b. When the flexible tensioning element 1202a is driven, a distal end component to which the flexible tensioning element 1202a is connected moves in a degree of freedom in a first direction. When the flexible tensioning element 1202b is driven, the distal end component to which the flexible tensioning element 1202b is also connected moves in the degree of freedom in a second direction. In this regard, the flexible tensioning elements 1202a, 1202b are driven in a manner to precisely control, for example, bi-directional movement of the distal end component in the degree of freedom.

FIGS. 12A to 12C depict mechanisms in which the flexible tensioning elements 1202a, 1202b are driven by separate drive components. In some implementations, as shown in FIG. 12A, the drive system 112 applies forces to drive components 1204a, 1204b. The first and second drive components are configured to translate when forces are applied to them, e.g., translate in a manner to apply tension to the flexible tensioning elements 1202a, 1202b. The drive system 112, for instance, translates a first drive input to apply a force 1206a to the flexible tensioning element 1202a, and translates a second drive input to apply a force 1206b to the flexible tensioning element 1202b. By applying the force 1206a, the drive system 112 drives the drive component 1204a to move proximally to apply a tension to the flexible tensioning element 1202a. By applying the force 1206b, the drive system 112 drives the drive component 1204b to move proximally to apply a tension to the flexible tensioning element 1202b. The drive system 112 applies the forces 1206a, 1206b in a manner to control movement of the distal end component, e.g., applies the force 1206a to move the distal end component in the first direction in the degree of freedom, and applies the force 1206b to move the distal end component in the second direction in the degree of freedom.

Rather than translating due to forces applied by the drive system 112, in some cases, as shown in FIG. 12B, drive components 1208a, 1208b rotate about rotational centers 1210a, 1210b, respectively, in response to the forces applied by the drive system 112. The drive components 1208a, 1208b are, for example, levers rotatable about the rotational centers 1210a, 1210b respectively. The flexible tensioning elements 1202a, 1202b are attached to the drive components 1208a, 1208b, respectively, such that distally directed forces 1211a, 1211b applied to the levers result in proximally directed forces, e.g., tensions, to be applied to the flexible tensioning elements 1202a, 1202b, respectively. The drive component 1208a applies a tension 1212a to the flexible tensioning element 1202a when the drive component 1208a is rotated, e.g., rotated counterclockwise about the rotational center 1210a as shown in FIG. 12B. The drive component 1208a rotates, and hence applies the tension 1212a, in response to the force 1211a applied by the drive system 112. The drive component 1208b applies a tension 1212b to the flexible tensioning element 1202b when the drive component 1208b is rotated, e.g., rotated clockwise about the rotational center 1210b as shown in FIG. 12B. The drive component 1208*b* rotates, and hence applies the tension 1212*b*, in response to the force 1211*b* applied by the drive system 112.

Rather than applying a force to rotate the drive components, in some cases, as shown in FIG. 12C, the drive system 112 applies torques 1216*a*, 1216*b* to rotate drive components 1218*a*, 1218*b*, respectively. The drive components 1218*a*, 1218*b* are, for example, rotatable capstans to which the flexible tensioning elements 1202*a*, 1202*b* are attached. The capstans, when rotated due to the torques 1216*a*, 1216*b*, apply tensions 1219*a*, 1219*b* to the flexible tensioning elements 1202*a*, 1202*b*, respectively. The drive component 1218*a* rotates in response to the drive system 112 applying the torque 1216*a*, and the drive component 1218*b* rotates in response to the drive system 112 applying the torque 1216*b*. When the drive components 1218*a*, 1218*b* rotate, the flexible tensioning elements 1202*a*, 1202*b* are wrapped around the drive components 1218*a*, 1218*b* such that the tensions 1219*a*, 1219*b* are applied to the flexible tensioning elements 1202*a*, 1202*b*.

In some cases in which the flexible tensioning elements 1202*a*, 1202*b* are attached to separate drive components, for example, as described with respect to FIGS. 12A-12C, to move the distal end component in a first direction, one of the drive components is driven to apply the tension to one of the flexible tensioning elements while the other of the drive components is operated in a manner to maintain minimal tension in the other of the flexible tensioning elements. The minimal tension is applied to the other of the flexible tensioning elements to avoid slack. The tension is applied to the flexible tensioning element to move the distal end component in a first direction. Furthermore, the other of the flexible tensioning element is relaxed to avoid impeding movement of the distal end component in the first direction. On the other hand, to move the distal end component in a second direction, the other of the flexible tensioning elements is driven. The flexible tensioning element is relaxed to avoid impeding movement of the distal end component in the second direction.

In some implementations, rather than being attached to separate drive components, the flexible tensioning elements are attached to the same drive component. Such examples are illustrated in FIGS. 12D and 12E. In some cases, as shown in FIG. 12D, the drive system 112 applies forces 1220*a*, 1220*b* to a single drive component 1222 to apply tensions to the flexible tensioning elements 1202*a*, 1202*b* attached to the drive component 1222. The drive component 1222 rotates about a rotational center 1223 when the drive component is driven by the forces 1220*a*, 1220*b*, rotating in a first direction in response to the force 1220*a* and rotating in a second direction in response to the force 1220*b*. The force 1220*a* drives the flexible tensioning element 1202*b* and relaxes the flexible tensioning element 1202*a*, and the force 1220*b* drives the flexible tensioning element 1202*a* and relaxes the flexible tensioning element 1202*a*. The drive component is, for example, a lever to which the flexible tensioning elements 1202*a*, 1202*b* are attached, the flexible tensioning elements 1202*a*, 1202*b* attached to opposing lever arms of the lever, e.g., lever arms extending away from the rotational center 1223 in opposite directions.

Rather than applying forces to move the drive component, in some cases, as shown in FIG. 12E, the drive system 112 applies a torque 1224 to a single drive component 1226 to drive the flexible tensioning element 1202*b*. The torque 1224 causes the flexible tensioning element 1202*a* to relax. The drive system 112 applies a torque in an opposite direction of the torque 1224 to the drive component 1226 to drive the flexible tensioning element 1202*a*. Such a torque causes the flexible tensioning element 1202*b* to relax. The single drive component 1226 is, for example, a rotatable capstan.

Referring back to FIG. 1, if the drive component 104*a* is coupled to multiple flexible tensioning elements, when the drive component 104*a* is driven in a first direction, the drive component 104*a* applies an actuation tension load to one of the flexible tensioning elements to move the distal end effector in a first direction. The other of the flexible tensioning elements, in some cases, relaxes. When the drive component 104*a* is driven in a second direction, the drive component 104*a* applies an actuation tension load to the other of the flexible tensioning elements to move the distal end effector in a second direction. The two flexible tensioning elements are, for example, wrapped in opposite directions around the drive component 104*a*. In some implementations, the flexible tensioning elements, when driven, apply a load to move the distal end component at a joint so as to move the distal end component in a clamping motion, a pitch motion, a yaw motion, a roll motion, etc.

When one of the flexible tensioning elements is driven and the other is relaxed, to prevent the relaxed flexible tensioning element from experiencing unacceptably low tension or slack, the flexible tensioning elements can be preloaded with a tension so that an acceptable minimum tension always exists on a tensioning element during instrument operation. For example, the acceptable minimum tension is equal to or greater than minimum tension used in the flexible tensioning elements during steering of the distal end component. As a result, when an actuation tension in one flexible tensioning element is applied, the other flexible tensioning element relaxes but does not become slack due to the applied actuation tension on the opposite tensioning element.

The surgical system 100 includes, in some examples, a controller 117. The controller 117 is configured to execute instructions stored on the memory 119 to perform operations, e.g., to control the drive system 112. The controller 117 operates the dynamic preload tensioner 116 such that the dynamic preload tensioner 116 moves, e.g., relative to the chassis 102, to adjust the path of the flexible tensioning element 106. The path adjustment, i.e., the increase in the path length, adjusts a tension in the flexible tensioning element 106. In some cases, the controller 117 operates an actuator of the drive system 112 to move the dynamic preload tensioner 116. The drive system 112 applies a load to the drive component 104*b*, which in turn applies a load to the dynamic preload tensioner 116. The dynamic preload tensioner 116, under the load applied by the drive component 104*b*, moves relative to the chassis 102.

The flexible tensioning element 106 is, for instance, a cable, a cable and hypotube combination, a wire, a filament, a bundle of filaments, braided filaments, a thread, a rope, twisted filaments, or other element in which a tension can exist. The flexible tensioning element 106, in some cases, is susceptible to creep, stress relaxation, or other changes in material properties of the flexible tensioning element 106. The flexible tensioning element 106 is formed from, for instance, a metal or a polymer. In cases in which the flexible tensioning element 106 is formed from a polymer, the flexible tensioning element 106 is, for instance, a polyethylene, a liquid crystal polymer, a polyester, etc.

In some implementations, the distal end component 108 is at a distal portion of a tubular member 115 attached to the chassis 102. The tubular member 115 is, for example, a shaft of a minimally invasive surgical instrument. The tubular member 115 is, for instance, an elongate body through which the flexible tensioning element 106 extends. The tubular member 115 extends distally from the chassis 102. A distal end of the tubular member 115 is coupled to the distal end component 108. The tubular member 115 contains at least a portion of the path of the flexible tensioning element 106. The tubular member 115, for instance, contains the flexible tensioning element 106 as the flexible tensioning element 106 extends from the chassis 102 to the distal end component 108. The tubular member 115, in some cases, supports the distal end component 108 to fix the position of the distal end component 108 relative to the chassis 102 as a load is applied to the flexible tensioning element 106 to steer the distal end component 108.

In some implementations, the dynamic preload tensioner 116 is movable between a first position 118 (shown in FIG. 1 as solid lines) and a second position 120 (shown in FIG. 1 as dashed lines). The dynamic preload tensioner 116 is, for example, movable to any position in a range of positions between the first position 118 and the second position 120. In some cases, the first position 118 corresponds to an initial position of the dynamic preload tensioner 116, e.g., the position of the dynamic preload tensioner 116 after the manufacturing of the surgical instrument 101 is complete, the position of the dynamic preload tensioner 116 absent operation of the dynamic preload tensioner 116. At the first position 118 of the dynamic preload tensioner 116, a first preload tension exists in the flexible tensioning element 106. At the second position 120 of the dynamic preload tensioner 116, a second preload tension exists in the flexible tensioning element 106. The second preload tension is larger than the first preload tension. In some cases, the first tension is zero. And in some cases, the first tension corresponds to an initial preload tension set during manufacture of the surgical instrument 101. The first tension is, for instance, a portion of the preload tension that exists in the flexible tensioning element 106 after the dynamic preload tensioner 116 is operated to cause the second tension.

In some implementations, the dynamic preload tensioner 116 is positioned to apply an adjustable preload tension to the flexible tensioning element 106 when the dynamic preload tensioner 116 moves to adjust the path of the flexible tensioning element 106. If an initial preload tension exists in the flexible tensioning element 106, the adjustable preload tension applied to the flexible tensioning element 106 results in an overall preload tension in the flexible tensioning element 106, corresponding to, for example, the sum of the adjustable preload tension and the portion of the initial preload tension in the flexible tensioning element 106.

Figure 2:
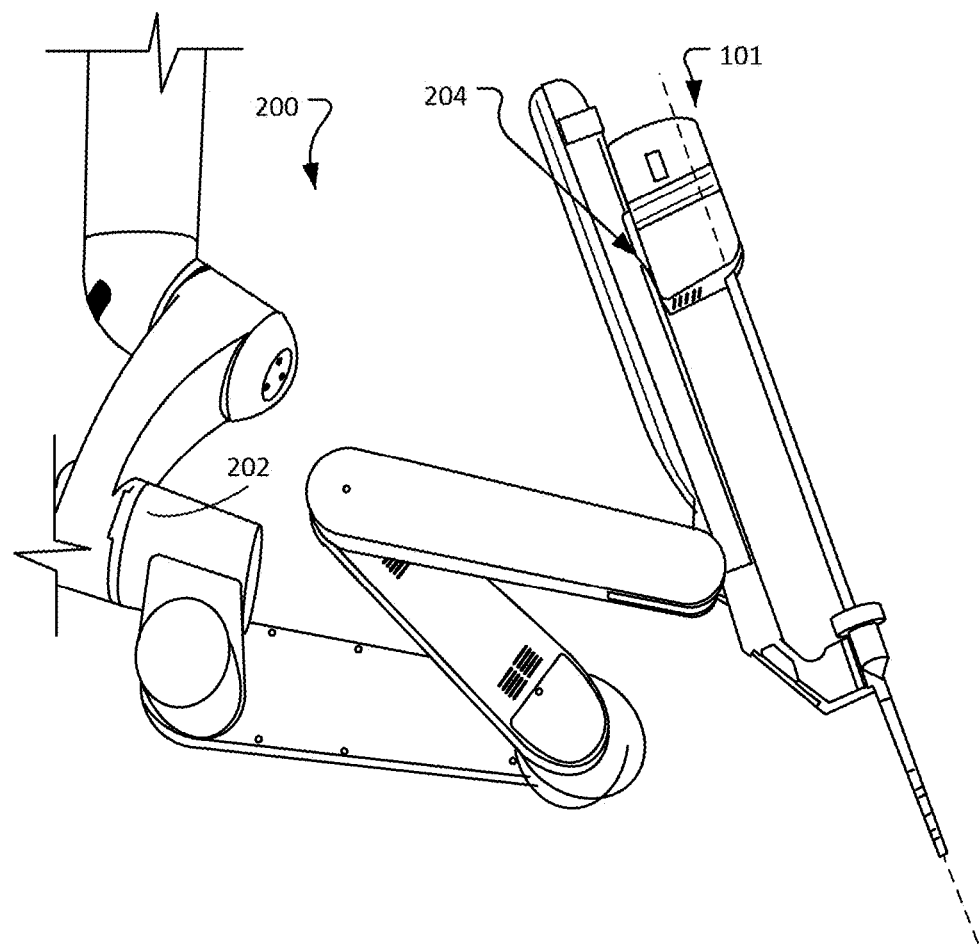
FIG. 2 is a side view of a surgical instrument mounted to a manipulator.

Referring to FIG. 2, in some implementations, the surgical instrument 101 is mounted to a manipulator 200. The manipulator 200 is, for example, a remotely controllable manipulator that can be operated by a surgeon at a location remote from the manipulator 200. The surgeon, for instance, operates control inputs on a console in communication with the manipulator 200, and the console generates control signals for a drive system of the manipulator 200 to control motion of the joints (e.g., joint 202) of the manipulator 200. The control signals, for instance, selectively activate actuators of the drive system of the manipulator 200. Such a surgical system architecture is known and can be seen, for example, in the da Vinci® Surgical Systems commercialized by Intuitive Surgical, Inc., Sunnyvale, Calif., and in various patents, such as U.S. Pat. No. 6,246,200 B1 (filed Aug. 3, 1999), U.S. Pat. No. 6,331,181 B1 (filed Oct. 15, 1999), and U.S. Pat. No. 6,788,018 B1 (filed Dec. 20, 2001), all of which are incorporated herein by reference.

The manipulator 200 includes, for example, an instrument carriage 204 to which the surgical instrument 101 can be mounted. The instrument carriage 204, for example, releasably supports the surgical instrument 101. The instrument carriage 204 includes one or more actuators that are part of the drive system of the manipulator 200. The instrument carriage 204 is, for instance, a mechanical interface connecting the drive system of the manipulator 200 to driven components of the surgical instrument. In some cases, when the surgical instrument 101 is mounted to the instrument carriage 204, the drive system of the manipulator 200 engages with drive components 104a, 104b of the surgical instrument 101 such that activation of the drive system drives the drive components 104a, 104b. The drive system of manipulator 200, for instance, includes multiple independently controllable drive outputs that connect to the drive components 104a, 104b of the surgical instrument 101. In some examples, when the surgical instrument 101 is mounted to the instrument carriage 204, one drive output is positioned to drive the drive component 104a, and another one of the drive outputs is positioned to drive the drive component 104b.

The drive system of the manipulator 200, in some examples, corresponds to the drive system 112 described with respect to FIG. 1. As a result, the drive system of the manipulator 200 is operable with the drive components 104a, 104b, to apply a load to the flexible tensioning element 106 and/or to cause the dynamic preload tensioner 116 to move. A drive output, for example, of the drive system of the manipulator 200 is operably connected to the dynamic preload tensioner 116 such that the dynamic preload tensioner 116 moves relative to the chassis 102 when the drive output is activated.

Figures 3A, 3B:
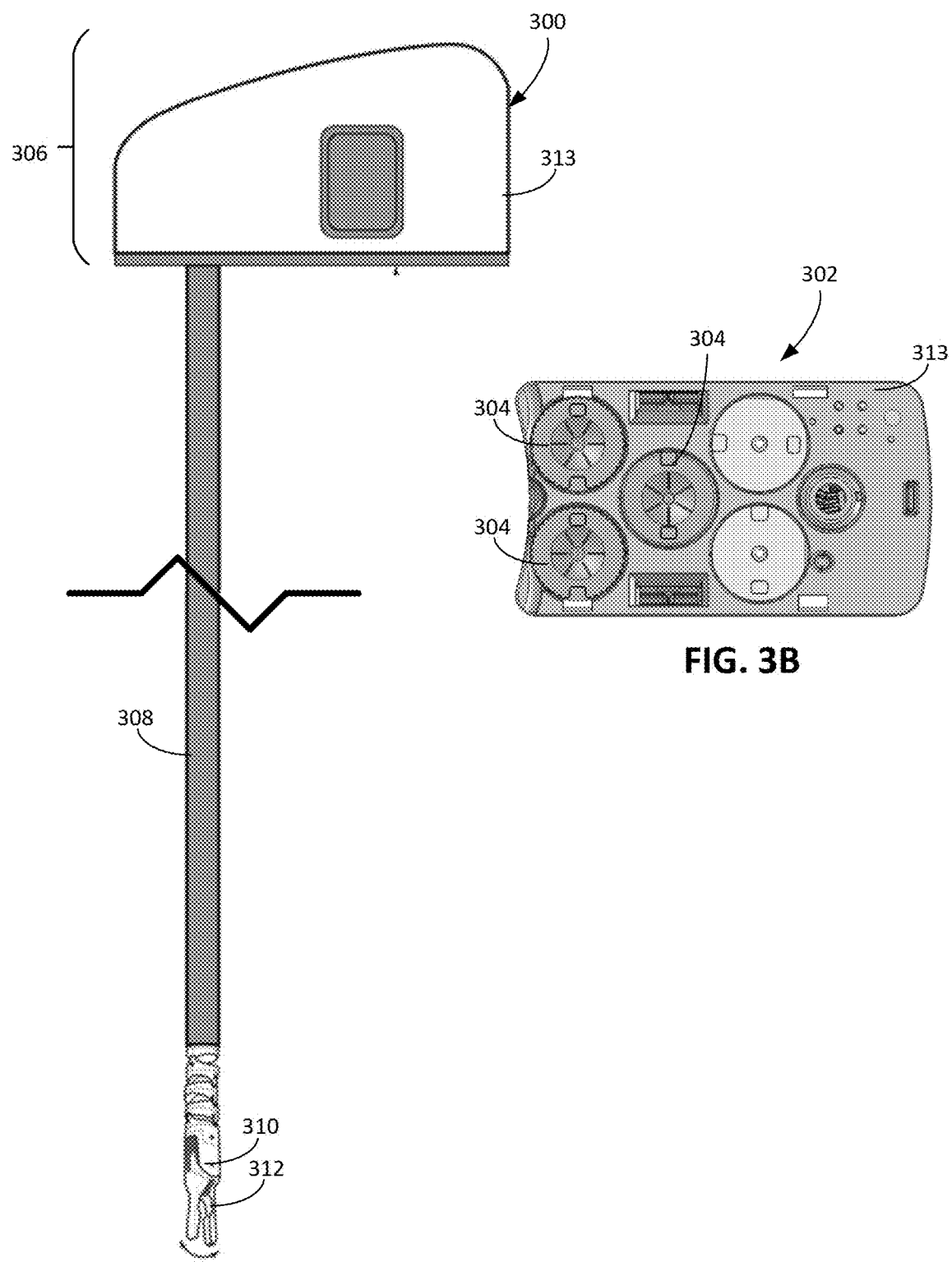
FIG. 3A is a side view of a surgical instrument.
FIG. 3B is a perspective view of a transmission unit of the surgical instrument of FIG. 3A.

FIG. 3A depicts another example of a surgical instrument 300 that can be mounted to the manipulator 200. The surgical instrument 300 includes a driven interface assembly 302, e.g., a mechanical interface to mechanically couple drive components 304 of the surgical instrument 300 with the drive system of the manipulator 200. The drive components 304 of the surgical instrument 300 include, for example, driven disks of the surgical instrument 300 that are rotatable by the drive system of the manipulator 200.

The surgical instrument 300 also includes a transmission unit 306, a tubular member 308 (e.g., the instrument shaft), a joint 310, and a distal end component 312. The transmission unit 306 transfers the loads applied by the drive system of the manipulator 200 to move the distal end component 312. The distal end component 312 is, for instance, an end effector that is operated during a surgical operation. The joint 310 is, for instance, a wrist joint that is movable to control an orientation of the distal end component 312.

In some implementations, the surgical instrument 300 includes flexible tensioning elements coupled to the drive components 304 mounted in a chassis 313 of the surgical instrument 300. As described with the flexible tensioning element 106 of FIG. 1, the flexible tensioning elements each extend along a path between a drive component and the distal end component. In some cases, multiple flexible tensioning elements extend from a single drive component to the distal end component 312 to control motion of the distal end component 312 along a degree of freedom.

The surgical instrument 300 includes one or more dynamic tensioners. In some implementations, the surgical instrument includes a single dynamic tensioner. One of the drive components 304 is coupled to the dynamic tensioner, and another one of the drive components is coupled to the flexible tensioning element, e.g., a proximal end of the flexible tensioning element. In implementations in which the surgical instrument includes multiple flexible tensioning elements, the single dynamic tensioner is movable relative to the chassis 313 to change a path of one, some, or all of the flexible tensioning elements.

In other implementations, the surgical instrument includes multiple dynamic tensioners. In these implementations, the surgical instrument includes, for example, a dynamic tensioner for each flexible tensioning element of the surgical instrument 300. Alternatively or additionally, the surgical instrument includes a dynamic tensioner associated with each drive component. Each dynamic tensioner, when its associated drive component is driven, adjusts the path of its associated flexible tensioning element. For example, one individual dynamic tensioner is positioned to controllably change the tension in a first flexible tensioning element, and a second individual dynamic tensioner is positioned to controllably change the tension in a second flexible tensioning element.

As shown in FIG. 13A, in some implementations, a first dynamic tensioner 1302*a* is positioned to engage a flexible tensioning element 1304*a*, and a second dynamic tensioner 1302*b* is positioned to engage a flexible tensioning element 1304*b*. The flexible tensioning elements 1304*a*, 1304*b* are driven to move a distal end component 1307 along a single degree of freedom, e.g., in a first direction if the flexible tensioning element 1304*a* is driven and in a second direction if the flexible tensioning element 1304*b* is driven. The first and second dynamic tensioners 1302*a*, 1302*b* are, for example, independently driven, e.g., operated by different drive components 1306*a*, 1306*b* and driven by different actuators of the drive system 112. In this regard, the preload tension applied to the first flexible tensioning element 1304*a* can be set in a manner independent from the preload tension applied to the second flexible tensioning element 1304*b*. In contrast, in some implementations as shown in FIG. 13B, a single dynamic tensioner 1308 is positioned to engage both of the flexible tensioning elements 1304*a*, 1304*b*. The dynamic tensioner 1308 is operated by a single drive component (not shown) and is driven by a single actuator of the drive system 112. In this regard, the drive system 112 operates a single dynamic tensioner 1308 to apply preload tensions to the flexible tensioning elements 1304*a*, 1304*b*.

The transmission unit 306 includes mechanical components, such as gears, levers, gimbals, cables, etc., to transfer loads from the drive components 304 of the surgical instrument 300 to the distal end component 312. The mechanical components of the transmission unit 306, for example, form a mechanism in the proximal portion of the surgical instrument 300 that mechanically couples the flexible tensioning elements of the surgical instrument 300 with the drive components 304 of the driven interface assembly 302.

In some implementations, the mechanical components mechanically couple a proximal end of a flexible tensioning element with one of the drive components, e.g., the drive component 104*a* of FIG. 1. Alternatively or additionally, the mechanical components mechanically couple a portion of the flexible tensioning element between distal and proximal ends of the flexible tensioning element and one of the drive components, e.g., the drive component 104*b* of FIG. 1. In such a case, the drive component, when driven, moves the dynamic tensioner to adjust the path of the flexible tensioning element, for example, by applying a transverse load on the flexible tensioning element.

If the drive components 304 include driven capstans, rotation of a driven capstan applies a tension load on a flexible tensioning element, e.g., pulls the flexible tensioning element. The flexible tensioning element then applies a load on a mechanical link in the distal end component 312 to move the distal end component 312, e.g., to reposition or to reorient a link of the distal end component 312.

The tubular member 308 is, in some cases, rigid. In some implementations, the tubular member 308 is bendable relative to the transmission unit 306. The tubular member 308 is, for example, elastically bendable such that the tubular member 308 returns to its original shape upon removal of a force that bends the tubular member 308. In other instances, however, tubular member is flexible but does not return to its initial shape after being flexed until the controller generates commands to the manipulator to return the tubular member to the initial shape.

Figure 4:
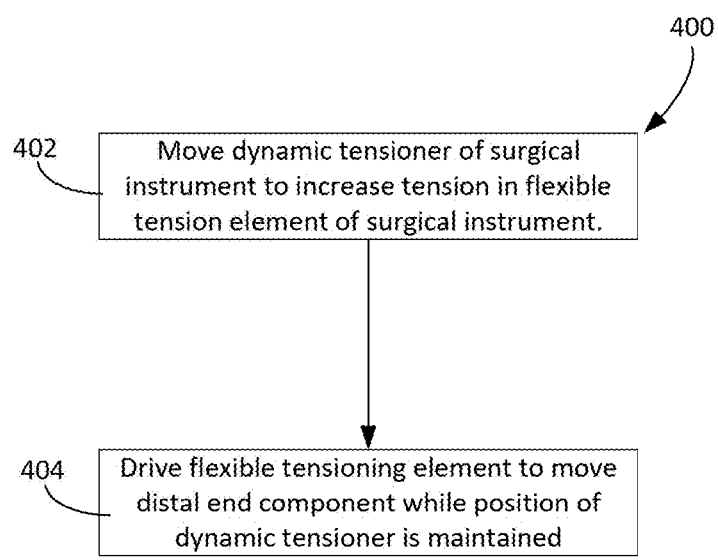
FIG. 4 is a process of operating a dynamic tensioner.

FIG. 4 depicts a flow chart of a process 400, e.g., performed by the controller 117, to operate a dynamic tensioner. The controller 117, for instance, performs the process 400 in connection with the surgical system 100 described with respect to FIG. 1.

At operation 402, the controller 117 moves a dynamic tensioner, e.g., the dynamic preload tensioner 116, of a surgical instrument, e.g., the surgical instrument 101, to increase tension in a flexible tensioning element, e.g., the flexible tensioning element 106, of the surgical instrument.

At operation 404, the controller 117 drives the flexible tensioning element to move a distal end component, e.g., the distal end component 108, while a position of the dynamic tensioner is maintained.

In some implementations, before moving the dynamic tensioner to increase the tension, the controller 117 receives information indicating that the surgical instrument has been mounted. The information, for instance, indicates that the surgical instrument has been mounted to a manipulator. In some examples, the controller 117 moves the dynamic tensioner when the controller 117 receives the information indicating that the surgical instrument has been mounted. In some implementations, the controller 117 receives information indicative of the predefined tension, e.g., a target value for a tension force in the flexible tensioning element. In some cases, the controller 117 determines when the tension in the flexible tensioning element has reached a predefined tension. The controller 117 maintains the position of the dynamic tensioner in response to determining that the tension in the flexible tensioning element has reached the predefined tension.

In some implementations, the controller 117 moves the dynamic tensioner of the surgical instrument by commanding drive system 112 to drive a corresponding drive component, e.g., the drive component 104*b*, to move the dynamic tensioner from a first position to a second position. In response to determining that the tension in the flexible tensioning element 106 has reached a predefined tension, the controller 117 maintains the position of the dynamic preload tensioner 116 such that the tension in the flexible tensioning element 106 is maintained at or above the predefined tension. If the controller 117 drives the drive component to move the dynamic tensioner, the controller 117 drives the drive component until the controller 117 receives the information indicating that the predefined tension is reached.

Alternatively or additionally, the controller 117 moves the dynamic tensioner of the surgical instrument while monitoring the tension in the flexible tensioning element. The controller 117, for instance, determines the tension of the flexible tensioning element 106 by monitoring the tension of the flexible tensioning element 106 during movement of the dynamic preload tensioner 116. In some implementations, to monitor the tension in the flexible tensioning element, the controller 117 receives information indicative of the tension in the flexible tensioning element. The information is, for instance, received from a sensor to measure in the flexible tensioning element. The sensor is, for example, a torque sensor associated with an actuator driving the drive component to drive the dynamic tensioner. The torque sensor generates a signal indicative of the torque applied by the actuator, and the controller 117, in some cases, determines the tension in the flexible tensioning element based on the torque. In some cases, the sensor is a torque sensor associated with an actuator driving the drive component to drive the flexible tensioning element. In an example, when the controller 117 drives a first drive component to move the dynamic tensioner to increase the tension in the flexible tensioning element, the controller 117 determines when torque measured by a torque sensor associated with a second drive component configured to drive the flexible tensioning element. The controller maintains the position of the first drive component after determining that the torque measured by the torque sensor is indicative of the tension in the flexible tensioning element reaching the predefined tension. Various other sensors may be used to sense tension in the flexible tensioning element, such as various types of strain or torque sensors mounted on a corresponding drive component or other component in the drive train associated with the flexible tensioning element.

In some implementations, the controller 117 drives the flexible tensioning element by driving a drive component, e.g., the drive component 104a. In this regard, the controller 117, in some cases, drives one drive component to move the dynamic tensioner and drives a second drive component to drive the flexible tensioning element to move the distal end component.

FIGS. 5A-11B depict a variety of examples of dynamic tensioners that change a path of a flexible tensioning element of a surgical instrument when operated. In each of these examples and other examples described herein, the path of the flexible tensioning element is changed by operation of a dynamic tensioner via a controller. In some cases, the dynamic tensioner applies a transverse load on the flexible tensioning element that adjusts the path of the flexible tensioning element. In some cases, the dynamic tensioner causes an axial load to be applied to the flexible tensioning element to adjust the path of the flexible tensioning element. This axial load is independent from the axial load applied to the flexible tensioning element to steer the distal end component. The path change of the flexible tensioning element results in the flexible tensioning element experiencing a tension, e.g., a preload tension. The dynamic tensioner is operable to generate an adjustable preload tension on the flexible tensioning element such that the preload tension can be applied or can be released. When the adjustable preload tension reaches a desired level, the preload tension can be locked to maintain the adjustable dynamic preload tension at the desired level while the flexible tensioning element is driven to steer the distal end component. Such tension locking may be done by keeping a dynamic preload tensioner in position once a desired preload tension value is established in a tensioning element, or by actively sensing tension in a tensioning element and continuing to dynamically adjust a dynamic tensioner to maintain the desired preload tension.

As described with respect to the example of FIG. 1, the path of the flexible tensioning element is changed to apply the preload tension to the flexible tensioning element. In some implementations, the path is lengthened by extending a portion of the path longitudinally. In some implementations, the path is lengthened by adjusting an angle between a first portion of a path and a second portion of a path. In some implementations, the path is lengthened by adding a bend in the path, e.g., by bending the flexible tensioning element.

Figure 5A:
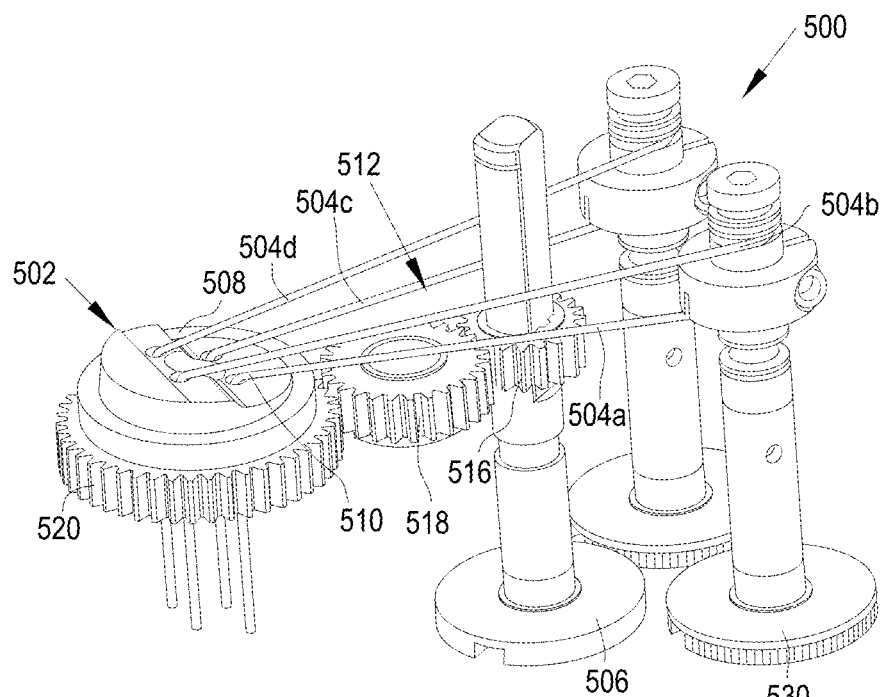
FIG. 5A is a top perspective view of a dynamic tensioner.
Figure 5B:
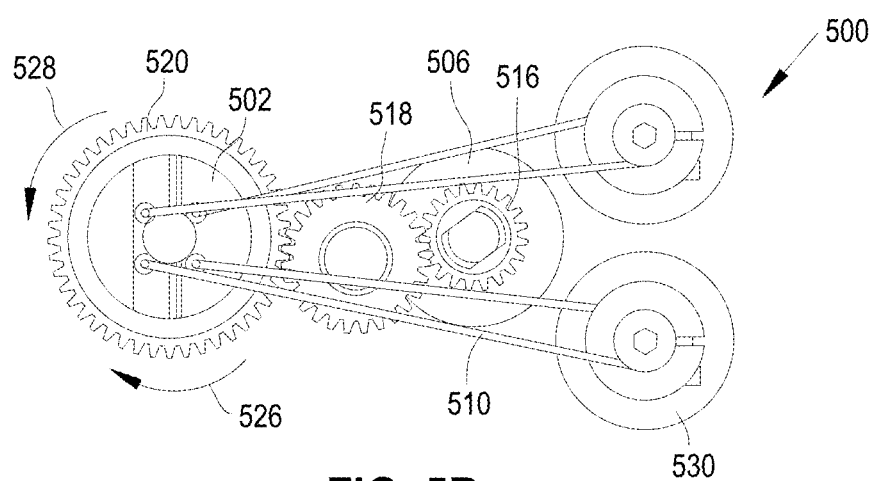
FIG. 5B is a top view of the dynamic tensioner of FIG. 5A.

FIGS. 5A and 5B depict an example of a dynamic tensioner 500 for a surgical instrument, the dynamic tensioner including a tensioning drum 502 positioned to engage a flexible tensioning element 504a. The tensioning drum 502 is axially movable such that it engages the flexible tensioning element 504a and changes the path of the flexible tensioning element 504a. In some examples, the tensioning drum 502 is axially movable relative to the chassis of the surgical instrument. The tensioning drum 502 is, for example, a cylindrical member movable along its central axis and positioned to engage the flexible tensioning element 504a as it moves along the central axis.

In some implementations, to change the path of the flexible tensioning element 504a, the tensioning drum 502 redirects a path of the flexible tensioning element 504a as the tensioning drum 502 moves to engage the flexible tensioning element 504a. The flexible tensioning element 504a extends along a first portion of its path from a drive component 506 to the tensioning drum 502. The flexible tensioning element 504a then bears against the tensioning drum 502, e.g., a top surface 508 of the tensioning drum 502, such that the path of the flexible tensioning element 504a is redirected. In particular, the path is redirected toward a distal end component of the surgical instrument. In some cases, the tensioning drum 502 includes an aperture 510 through which the flexible tensioning element 504a is routed. The path of the flexible tensioning element 504a extends from the drive component 506 toward the aperture 510, then through the aperture 510 while the flexible tensioning element 504a bears against the top surface 508 of the tensioning drum 502. The path of the flexible tensioning element 504a then extends toward a joint of the distal end component.

As the tensioning drum 502 moves axially, the tensioning drum 502, e.g., the top surface 508 of the tensioning drum 502, engages the flexible tensioning element 504a and causes the flexible tensioning element 504a to move with the tensioning drum 502. Because the flexible tensioning element 504a bears against the tensioning drum 502, movement of the tensioning drum 502 causes the path of the flexible tensioning element 504a to change. In some implementations, the movement of the tensioning drum 502 causes the path change by repositioning a bending point of the path, e.g., a point at which the path of the flexible tensioning element 504a is redirected.

In some implementations, to move the tensioning drum 502, the dynamic tensioner 500 includes a drive mechanism 512 that, when driven, causes the axial movement of the tensioning drum 502. The drive mechanism 512, includes the drive component 506 driven by, e.g., the drive system of the manipulator 200. The drive component 506 transfers the load through a gear system. In some examples, as the drive component 506 is driven to rotate, a gear 516 coupled to the drive component 506 is driven to rotate a gear 518, which in turn rotates a tensioning gear 520. The tensioning gear 520, when rotated, drives the tensioning drum 502 to move axially relative to the tensioning gear 520. The gear 516, the gear 518, and the tensioning gear 520 are each rotatably mounted to the chassis of the surgical instrument.

Figure 5C:
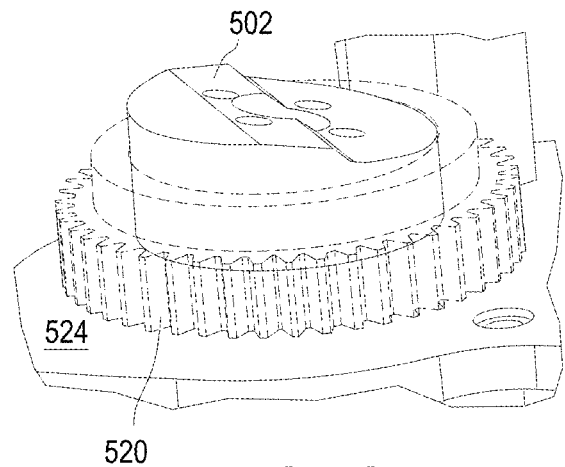
FIG. 5C is a top perspective view of a tensioning drum of the dynamic tensioner of FIG. 5A.
Figure 5D:
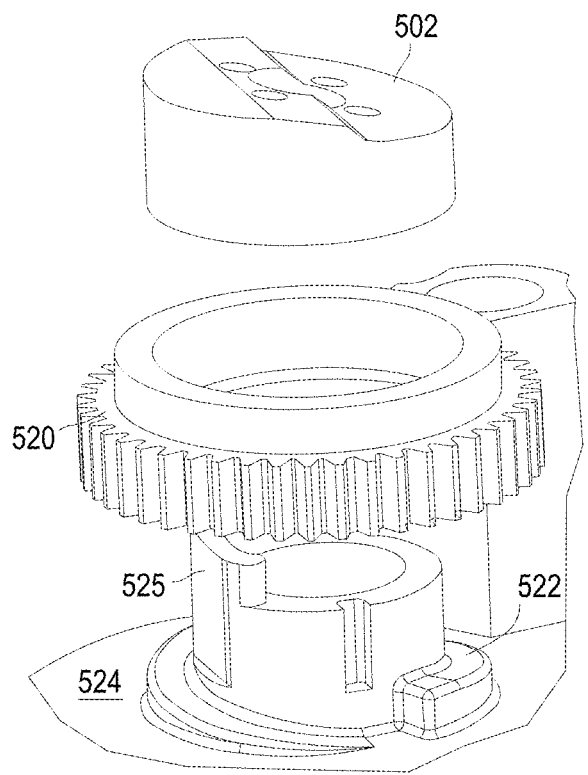
FIG. 5D is a top perspective exploded view of the tensioning drum of the dynamic tensioner of FIG. 5C.

Referring to FIGS. 5C and 5D, the tensioning gear 520, for instance, bears against a ramp 522 defined by the chassis, e.g., formed on a surface 524 of the chassis of the surgical instrument. The ramp 522 increases in height relative to the surface 524 in the clockwise direction, as depicted in FIG. 5D. A top surface of the ramp 522, for instance, follows a helical path extending away from the surface 524 of the chassis. The tensioning gear 520 follows the helical path as the tensioning gear 520 is rotated along the ramp 522. The tensioning drum 502 is coupled to the tensioning gear 520 such that the tensioning drum 502 moves axially when the tensioning gear 520 is rotated along the ramp 522 of the chassis of the surgical instrument.

In some implementations, the tensioning drum 502 is keyed to the chassis such that the tensioning drum 502 does not rotate as the tensioning gear 520 rotates. Referring to FIG. 5D, the tensioning drum 502 is keyed to a locking element 525 of the chassis that engages with a corresponding locking element on a bottom surface of the tensioning drum 502. The locking element 525 is, for instance, a protrusion that extends through the tensioning gear 520 and engages with a corresponding bore on the bottom surface of the tensioning drum 502. Alternatively, the locking element 525 is a bore that engages with a corresponding protrusion on the bottom surface of the tensioning drum 502. Engagement between the locking element 525 and the corresponding locking element on the tensioning drum 502 inhibits relative rotation of the chassis and the tensioning drum 502 such that, as the tensioning gear 520 rotates, the tensioning drum 502 does not rotate. Instead, both the tensioning gear 520 and the tensioning drum 502 move axially as the tensioning gear 520 rotates.

The axial position of the tensioning drum 502 relative to the surface 524 of the chassis depends on a rotational position of the tensioning gear 520 relative to the surface 524 of the chassis. As the tensioning gear 520 is rotated in a first direction 526, the length of the path of the flexible tensioning element 504a increases and the tension existing in the flexible tensioning element 504a increases. Because of the slope of the ramp 522 bearing against the tensioning gear 520, the tensioning gear 520 and the tensioning drum 502 move axially away from the surface 524 of the chassis as the tensioning gear 520 rotates in the first direction. In contrast, the tensioning drum 502 and the tensioning gear 520 move axially toward the surface 524 of the chassis as the tensioning gear 520 rotates in the second direction 528. In this regard, as the tensioning gear 520 is rotated in the second direction 528, the tension existing in the flexible tensioning element 504a decreases.

While described in terms of a single flexible tensioning element 504a, in some implementations, as shown in FIGS. 5A and 5B, the tensioning drum 502 is positioned to engage with multiple flexible tensioning elements 504a-504d. In this regard, axial movement of the tensioning drum 502 changes a path of each of the flexible tensioning elements 504a-504d. In some implementations, as shown in FIG. 5A, in addition to the drive component 506 driven to operate the dynamic tensioner 500, a drive component 530 is driven to apply a load to the flexible tensioning element 504a, e.g., to steer the distal end component. As described herein, a drive system of a remotely controllable manipulator can drive the drive component 530. In some cases, the drive component 530 is coupled to multiple flexible tensioning elements, e.g., the flexible tensioning elements 504a, 504b. As the drive component 530 is driven, the drive components 530 applies tension to one of the flexible tensioning elements 504a, 504b while releasing tension to the other of the flexible tensioning elements 504a, 504b. The loads applied to the flexible tensioning elements 504a, 504b, for example, control motion of the distal end component along a single degree of freedom. The drive component 530, in some example, drives the flexible tensioning element 504b such that the flexible tensioning element 504a is relaxed when the flexible tensioning element 504b is driven, and such that the flexible tensioning element 504b is relaxed when the flexible tensioning element 504a is driven. The preload tension applied by the dynamic tensioner 500 to the flexible tensioning elements 504a, 504b is sufficiently large such that the flexible tensioning elements 504a, 504b do not become slack as they relax during operation of the drive component 506.

The drive component 506 is, for instance, a capstan that is rotatable by an actuator of the drive system of the manipulator. In some implementations, a torque on the capstan is determined, e.g., by the controller 117, based on a current applied to the actuator to cause the capstan to rotate. The controller 117 in turn determines the force applied by the tensioning drum 502 on the flexible tensioning element 504a.

In some examples of a dynamic tensioner, the dynamic tensioner includes a spring to apply a static preload tension to the flexible tensioning element. The static preload tension is, for instance, a non-adjustable preload tension applied to the flexible tensioning element that maintains relative positions of components of the surgical instrument, e.g., mechanical integrity. During a surgical operation, the dynamic tensioner is operated to set an adjustable preload tension for the flexible tensioning element that is in addition to the preload tension caused by the spring. In some implementations, the spring is configured such that a force from the flexible tensioning element on the dynamic tensioner, e.g., due to a load applied to the flexible tensioning element to steer the distal end component, is not absorbed by the spring. When an actuation tension load is applied to the flexible tensioning element to steer the distal end component, the actuation load on the flexible tensioning element, rather than being absorbed by the spring, is transferred to the distal end component, e.g., is transferred to move the distal end component. In some cases, the dynamic tensioner, when operated, compresses the spring to cause the coils of the spring to contact one another such that, when the adjustable preload tension is applied using the dynamic tensioner, the spring cannot further absorb a force applied by the flexible tensioning element during steering of the distal end component. Likewise, in some cases, the dynamic tensioner, when operated causes the spring to disengage from a portion of the dynamic tensioner, e.g., the portion bearing against the flexible tensioning element, such that a force of the flexible tensioning element on the portion of the dynamic tensioner is not absorbed through compression of the spring.

Figure 5E:
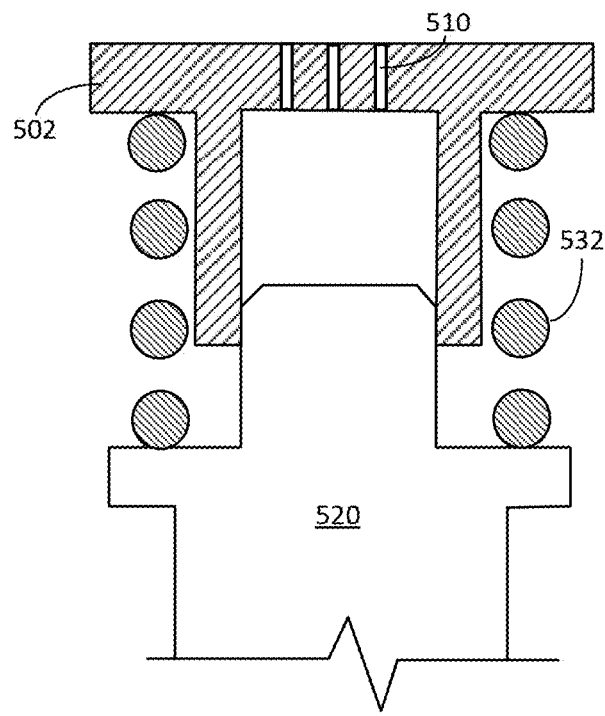
FIG. 5E is a side schematic view of the dynamic tensioner of FIG. 5A including a spring in an expanded position.
Figure 5F:
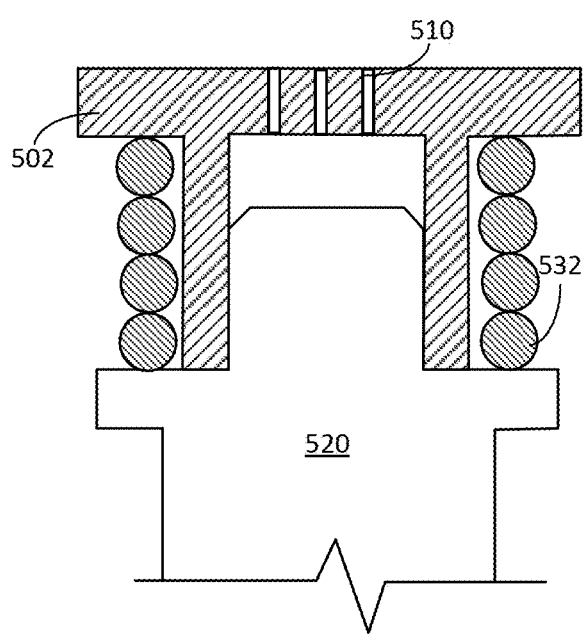
FIG. 5F is a side schematic view of the dynamic tensioner of FIG. 5E with the spring in a compressed position.

Referring to FIG. 5E, in the example of the dynamic tensioner 500 including the tensioning drum 502, in some examples, the dynamic tensioner 500 includes a spring 532 that applies a static preload tension. FIG. 5E shows the spring 532 in an expanded position in which the spring 532 applies the static preload tension to the flexible tensioning element. The spring 532, for instance, is positioned between the tensioning drum 502 and the tensioning gear 520. When the tensioning gear 520 is rotated, the tensioning gear 520 advances toward the tensioning drum 502 to compress the spring 532. Referring to FIG. 5F showing the spring 532 in a compressed position, in the process of moving the tensioning drum 502, the tensioning gear 520 compresses the spring 532 beyond a linear elastic range, e.g., such that the coils of the spring 532 contact one another. When the spring 532 is compressed in this manner, the static preload tension in the flexible tensioning element 504a caused by the spring 532 does not increase as the tensioning drum 502 is moved axially to increase the adjustable preload tension. The tensioning drum 502 is moved to change the path of the flexible tensioning element 504a while the coils of the spring 532 contact one another.

Figure 6:
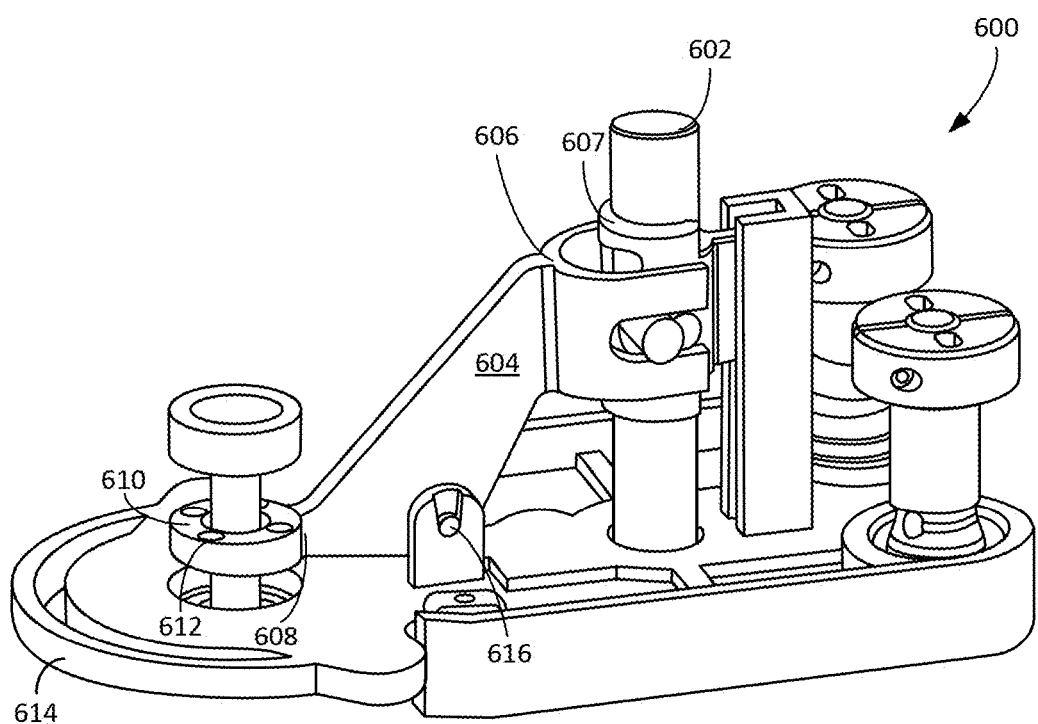
FIG. 6 is a top perspective view of an example of a dynamic tensioner.

Referring to the example of a dynamic tensioner 600 shown in FIG. 6, in some implementations, the dynamic tensioner 600 includes a lead screw 602 rotatable to adjust a path of the flexible tensioning element. The dynamic tensioner 600 includes an arm 604 with a first end 606 engaged to the lead screw 602. The first end 606 of the arm 604 is, for example, movable along a longitudinal axis of the lead screw 602. A nut 607 axially movable along the lead screw 602 couples the lead screw 602 to the first end 606 of the arm 604. A second end 608 of the arm 604 includes a guide 610 including an aperture 612 through which the flexible tensioning element extends. The arm 604 is pivotally mounted to the chassis 614 of the surgical instrument at a pin 616.

The lead screw 602, for instance, is coupled to a drive component to be driven by the drive system of the manipulator to which the surgical instrument is mounted. An input load, e.g., a torque, applied to the lead screw 602 rotates the arm 604 relative to the chassis, e.g., such that the arm 604 pivots about the pin 616 on the chassis. When driven, the lead screw 602 rotates. In some implementations, the nut 607 moves axially when the lead screw 602 rotates, thereby rotating the first end 606 of the arm 604 about the pin 616. The pivoting motion of the arm 604 then moves the second end 608 of the arm 604. In particular, the second end 608 rotates such that a path of the flexible tensioning element (not shown) routed through the guide 610 is adjusted. The guide 610, for example, bears against the flexible tensioning element such that movement of the guide 610 causes the path of the flexible tensioning element to be adjusted. The lead screw 602 is rotated to adjust the path of the flexible tensioning element, and hence to increase the tension in the flexible tensioning element. In some cases, the arm 604 applies a tension to the flexible tensioning element that increases nonlinearly with the torque applied to the lead screw 602.

The flexible tensioning element is, for example, attached to a drive component 603a. In some cases, multiple flexible tensioning elements are attached to the drive component 603a and routed through apertures 612 on the guide 610. The arm 604, when pivoted, causes the guide 610 to pivot and move proximally away from the distal component, thereby adjusting the path of each of the flexible tensioning elements. The lead screw 602, when rotated, applies preload tension to each of the flexible tensioning elements through manipulation of the guide 610. In some implementations, another set of flexible tensioning elements are attached to a drive component 603b. The guide 610, when pivoted, adjusts a path of each of the flexible tensioning elements. In some cases, the first set of flexible tensioning elements attached to the drive component 603a controls movement of the distal end component in one degree of freedom, and the second set of flexible tensioning elements attached to the drive component 603b controls movement of the distal end component in another degree of freedom.

In some examples of dynamic tensioners, the dynamic tensioner is driven by a drive component that, when operated, causes motion of the distal end component along a degree of freedom. The drive component is, for instance, a multi-functional drive component that is drivable to apply the adjustable preload tension and is also drivable to apply a load to steer the distal end component. In such cases, the manipulator to which the surgical instrument is mounted does not require a drive input to drive the dynamic tensioner independent from a drive input to steer the distal end component on the surgical instrument.

Figure 7A:
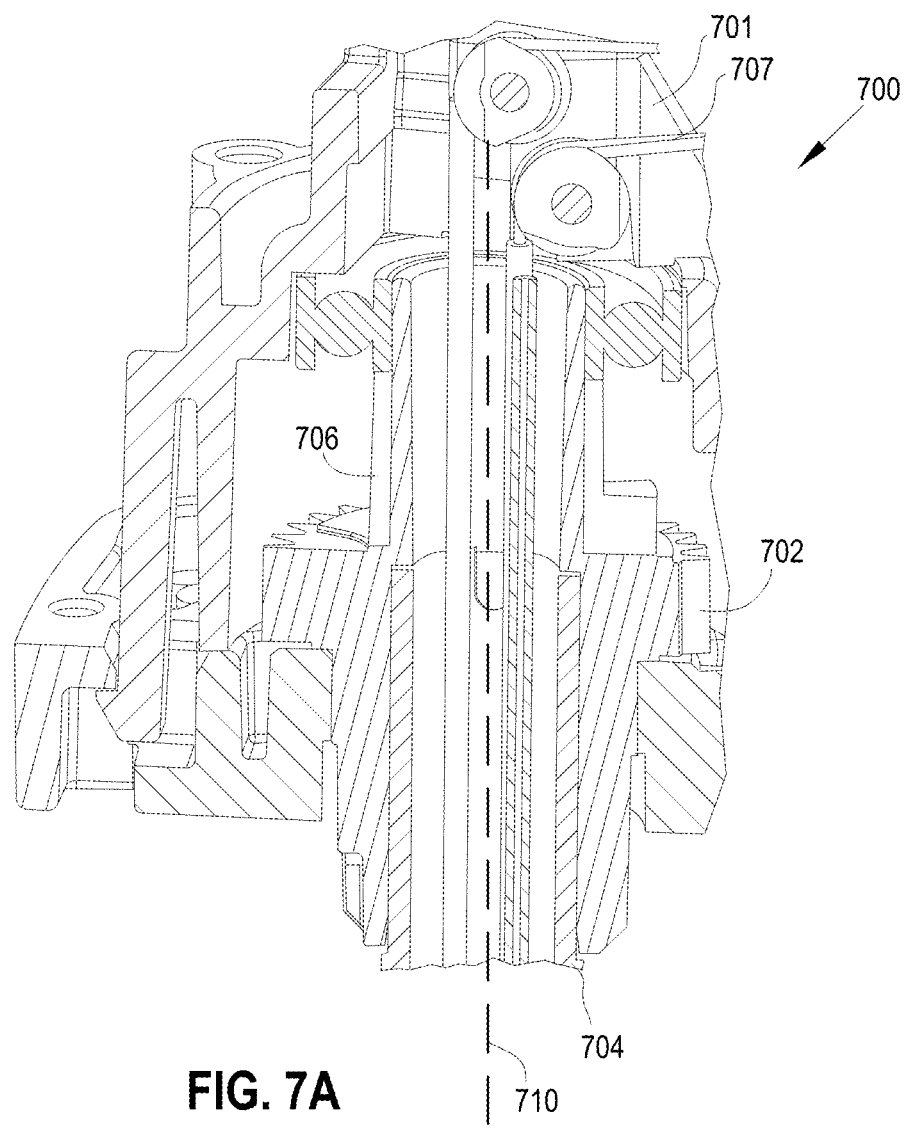
FIG. 7A is a side cross-sectional view of a dynamic tensioner.

FIG. 7A depicts an assembly that mounts the tubular member 704 of the surgical instrument to the chassis of the surgical instrument, e.g., mounts the tubular member 115 to the chassis 102. The assembly includes an assembly housing 701 that houses an example of a dynamic preload tensioner 700. The assembly housing 701 is, in some cases, part of the chassis of the surgical instrument. The dynamic tensioner 700 is associated with a mechanism to control motion along a roll degree of freedom of the distal end component, e.g., rotation of the distal end component about a longitudinal axis 710 of the tubular member 704. In some examples, a roll drive mechanism of the surgical instrument includes a gear 702 that, when driven, rotates the tubular member 704 coupled to the distal end component. The distal end component rotates, e.g., rolls about the longitudinal axis 710 of the tubular member 704, in response to rotation of the tubular member 704. The gear 702 is driven by a drive component that is, for example, coupled to a drive system of a manipulator.

Figure 7B:
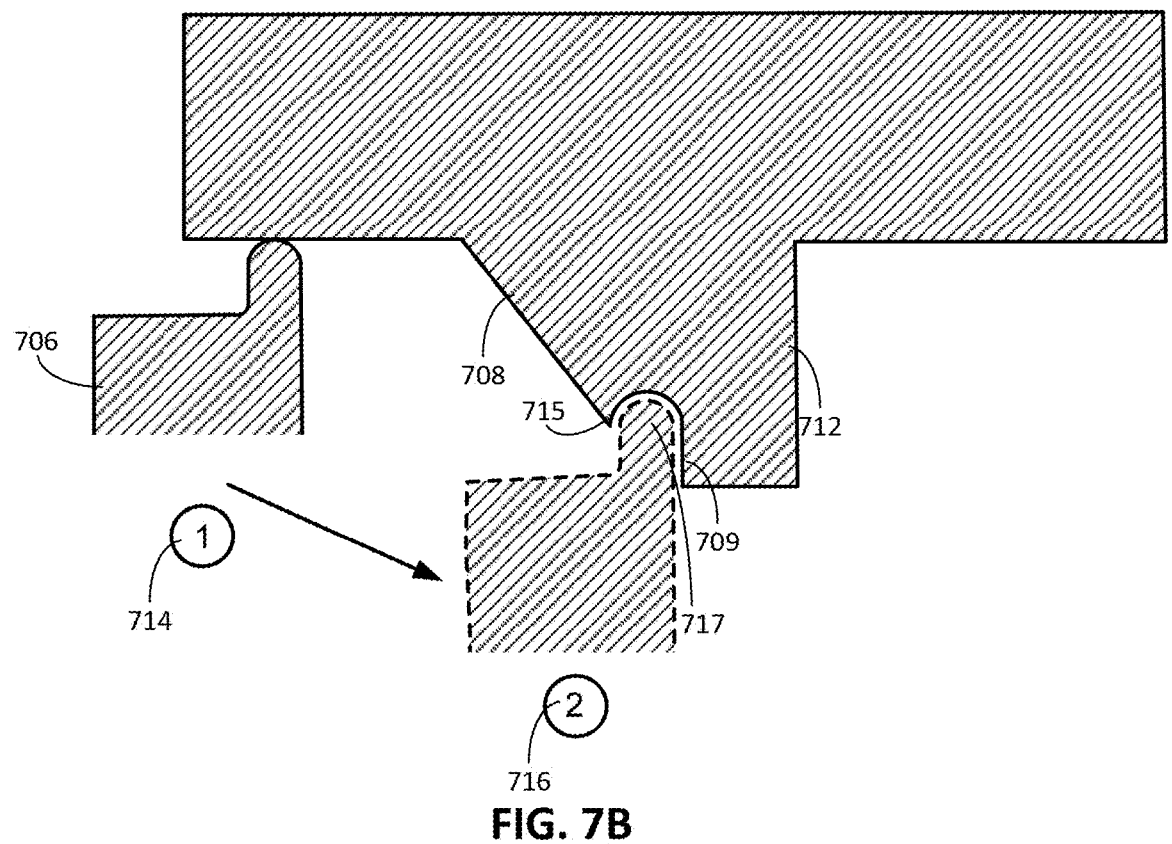
FIG. 7B is a side schematic view of a rotatable member of the dynamic tensioner of FIG. 7A in a first position and in a second position.

Referring also to FIG. 7B, the dynamic tensioner 700 includes a rotatable member 706. When the gear 702 is rotated to a predefined orientation, the gear 702 engages the rotatable member 706 such that the rotatable member 706 rotates relative to the assembly housing 701, e.g., rotates about the longitudinal axis 710 of the tubular member 704. The rotatable member 706 moves along the longitudinal axis 710 as the rotatable member 706 rotates relative to the assembly housing 701. The gear 702 and the tubular member 704 move axially when the rotatable member 706 rotates. The distal end component moves axially when the tubular member 704 moves axially.

The tubular member 704, as described herein, supports the distal end component and contains a portion of a path of a flexible tensioning element 707 coupled to the distal end component. In this regard, the path of the flexible tensioning element 707 is changed, e.g., a length of the path increases, when the tubular member 704 moves axially distally. In particular, the distal end component, in response to the axial movement of the tubular member 704, moves away from the assembly housing 701, thereby lengthening the path of the flexible tensioning element 707. In particular, the length of the portion of the path of the flexible tensioning element 707 between the assembly housing 701 and the distal end component extends due to the axial movement of the tubular member 704. The rotatable member 706, when rotated, thus causes a tension to be applied to the flexible tensioning element 707.

In some implementations, as the rotatable member 706 rotates, it follows a ramp 708, e.g., a helical path, such that the rotatable member 706 moves along the longitudinal axis 710. In some examples, the ramp 708 is formed on a delimiter member 712 in the assembly housing 701. The rotatable member 706 is rotatable relative to the delimiter member 712. The delimiter member 712 includes a delimiting portion 709 that, upon engaging with the rotatable member 706, inhibits further rotation of the rotatable member 706. The rotatable member 706 rotates along the ramp 708 about the longitudinal axis 710 and then contacts the delimiting portion 709, which inhibits further rotation of the rotatable member 706. Because the rotatable member 706 is rotated by the gear 702 driven to roll the distal end component, the delimiting portion 709, when engaged with the rotatable member 706, inhibits rotation of the gear 702 and thus inhibits further roll motion of the distal end component, e.g., rotation of the distal end component about the longitudinal axis 710 of the tubular member 704.

In some implementations, the rotatable member 706 is movable between a first axial position 714 and a second axial position 716. The tubular member 704 moves axially when the rotatable member 706 is moved from the first axial position 714 (proximal) to the second axial position 716 (distal). The axial movement of the tubular member 704 to the second axial position 716 extends the path of the flexible tensioning element 707. In some implementations, an initial preload tension is applied to the flexible tensioning element 707 when the rotatable member 706 is in the first axial position 714, and an operating preload tension greater than the initial preload tension is applied to the flexible tensioning element 707 when the rotatable member 706 is in the second axial position 716. The operating preload tension is, for example, a preload tension that facilitates one-to-one transfer of an actuating tension load from a proximal end of the flexible tensioning element 707 to a distal end of the flexible tensioning element 707, e.g., to the distal end component.

In some cases, the rotatable member 706 is lockable to the delimiter member 712. The rotatable member 706 is, for instance, lockable to the delimiter member 712 when the rotatable member 706 is moved to the second axial position 716. The rotatable member 706 includes, for instance, a locking portion 715 that engages a corresponding locking portion 717 of the delimiter member 712. When the locking portion 715 of the rotatable member 706 engages the corresponding locking portion 717 on the delimiter member 712, the rotatable member 706 is locked to the delimiter member 712 such that further rotation of the rotatable member 706 is inhibited. While first and second positions are described, in other implementations, the rotatable member 706 is lockable to one of multiple discrete positions. In this regard, one of multiple discrete preload tensions is applied to the flexible tensioning element 707 depending on the selected discrete position of the rotatable member 706.

In some implementations, the gear 702 is rotatable over a first predefined range to roll the distal end component. The gear 702 is also rotatable beyond the first predefined range into a second predefined range. When the gear 702 is rotated into the second predefined range, the gear 702 engages the rotatable member 706 to rotate the rotatable member 706 relative to the delimiter member 712. In this regard, the gear 702 does not rotate the rotatable member 706 while the gear 702 is rotated within the first predefined range. The first predefined range is, for instance, 180 degrees, e.g., the gear 702 rotates up to 90 degrees in a clockwise direction and up to 90 degrees in a counterclockwise direction from its initial position. The second predefined range is, for example, 20 to 40 degrees beyond the first predefined range. The gear 702, for instance, rotates 20 to 40 degrees past the first predefined range when the gear 702 is rotating in the second predefined range.

In some cases, the first predefined range is a controller-enforced range. In some cases, the controller, e.g., the controller 117, inhibits the gear 702 from moving beyond the first predefined range after the gear 702 is rotated such that the rotatable member 706 is locked in the second axial position 716 to apply a preload tension.

In some implementations in which the rotatable member 706 is lockable to the delimiter member 712, when the rotatable member 706 is locked to the delimiter member 712, the gear 702 is moved from the second predefined range back to the first predefined range such that the gear 702 can be driven to roll the distal end component. As a result, the gear 702 is drivable to cause the rolling motion of the distal end component while a preload tension is applied to the flexible tensioning element 707.

Figure 7C:
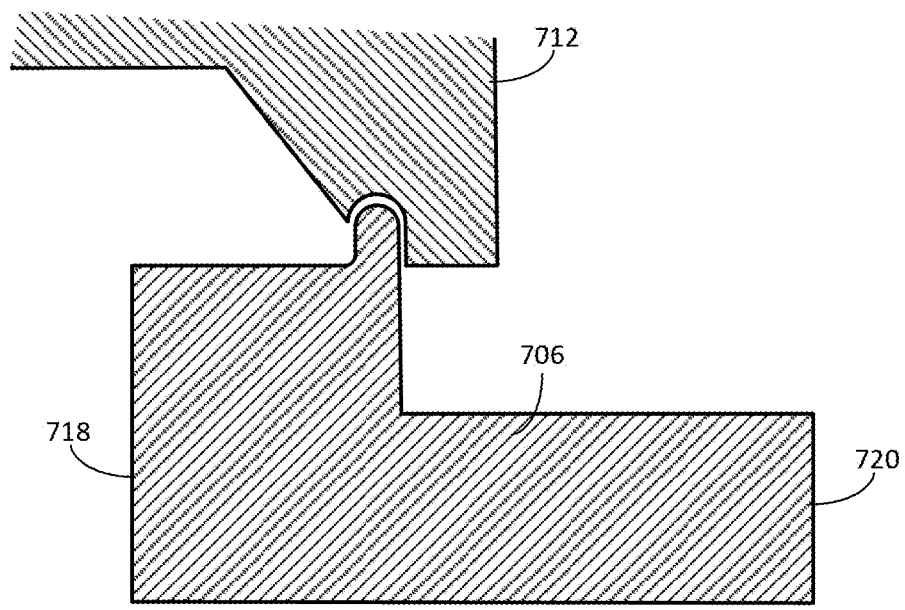
FIG. 7C is an example of a rotatable member of the dynamic tensioner of FIG. 7A.

Referring to FIG. 7C, in some implementations, the gear 702 contacts a first lateral portion 718 of the rotatable member 706 to rotate the rotatable member 706 from the first position toward its second position. The gear 702 contacts a second lateral portion 720 of the rotatable member 706 to rotate the rotatable member 706 from the second position back toward the first position. In such an example, the gear 702 engages the rotatable member 706 to reposition the rotatable member 706 toward the second position to apply the operating preload tension to flexible tensioning element 707. The gear 702 is also able to engage the rotatable member 706 to move the rotating member back toward the first position such that the preload tension is released.

Figure 8:
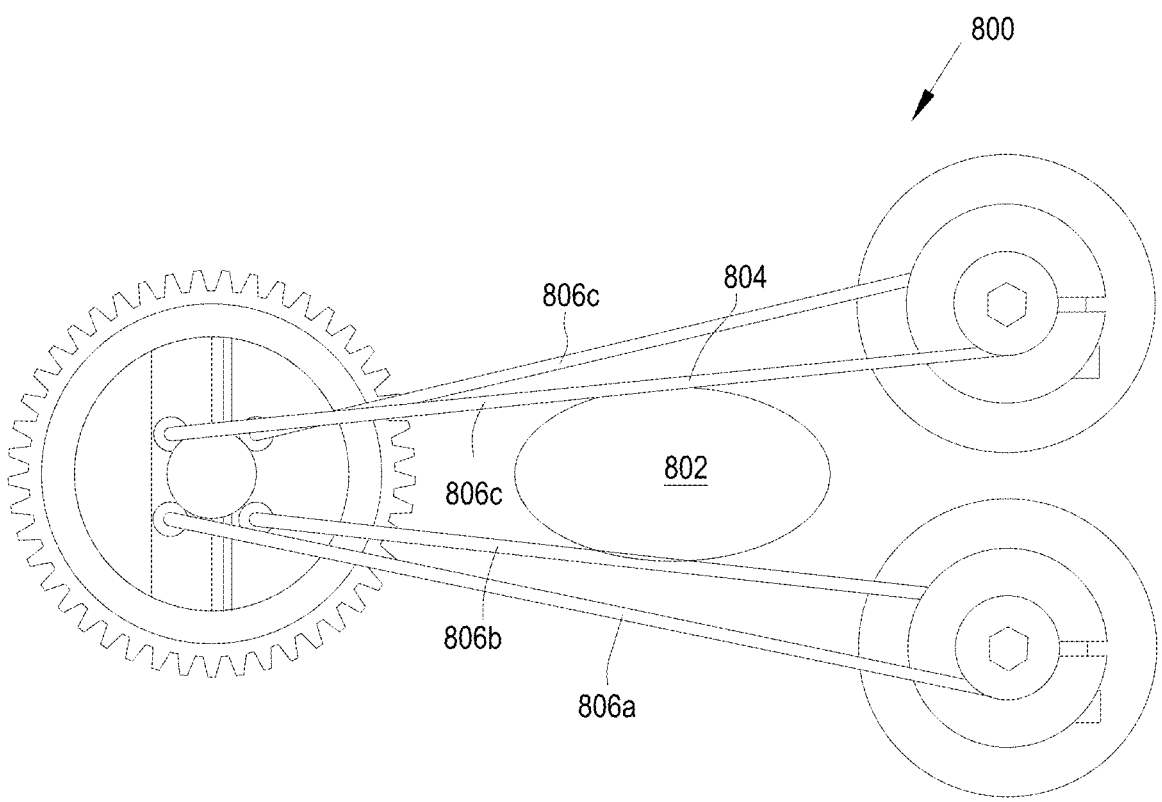
FIG. 8 is a top view of an example of a dynamic tensioner.

FIG. 8 depicts another example of a dynamic preload tensioner 800. The dynamic tensioner 800 includes a rotatable cam 802. The rotatable cam 802 is, for instance, coupled to a drive component of the surgical instrument such that the rotatable cam 802 rotates when the drive component is driven. In some cases, the rotatable cam 802 rotates relative to a chassis of surgical instrument. A surface 804 of the rotatable cam 802 engages a flexible tensioning element 806b to change the path of the flexible tensioning element 806b when the rotatable cam 802 is rotated. In some implementations, the surface 804 of the rotatable cam 802 engages each of multiple flexible tensioning elements 806a-806d when the rotatable cam 802 is rotated (i.e., for any rotation angle of the cam, the shape of the cam surface that engages elements 806a and 806d causes the same path length change as path length change caused by the shape of the cam surface that engages elements 806b and 806c). The rotatable cam 802 applies transverse loads on the flexible tensioning elements 806a-806d to deflect the flexible tensioning elements 806a-806d, thereby adjusting the paths of the flexible tensioning elements 806a-806d. In some cases, the surface 804 of the rotatable cam 802 is elliptical.

Figure 9A:
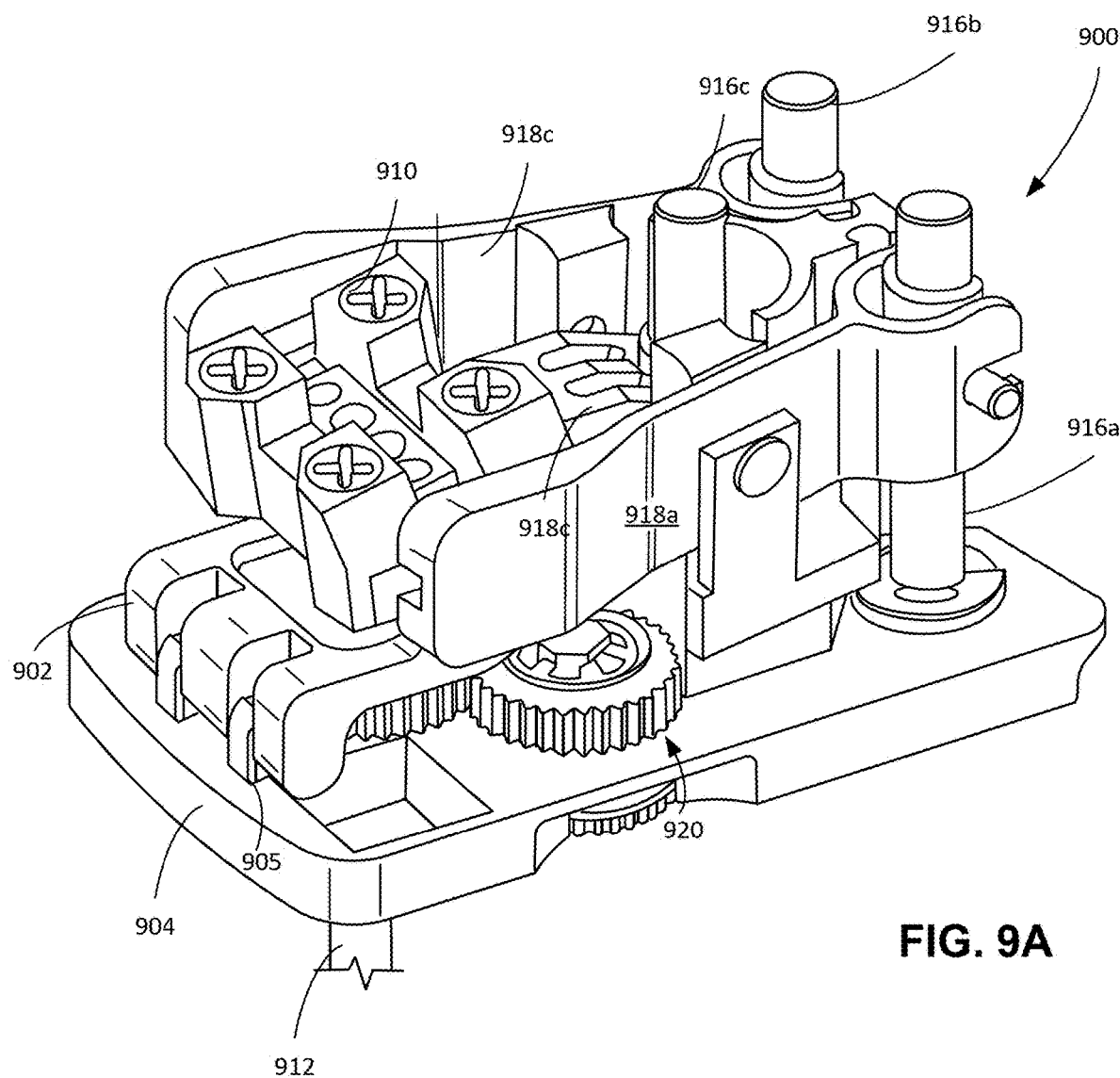
FIGS. 9A and 9B are left and right perspective side views, respectively, of an example of a dynamic tensioner.

FIG. 9 depicts an example of a dynamic preload tensioner 900 that includes a tensioning plate 902 pivotably mounted to the chassis 904 of the surgical instrument. The tensioning plate 902 is, for example, rotatable about a pin 905 on the chassis 904. When the tensioning plate 902 is rotated relative to the chassis 904, a path of a flexible tensioning element is changed.

In some implementations, the flexible tensioning element is routed from a gimbal 910 inward and through an aperture in tensioning plate 902, and then into the tubular member 912 to the distal end component of surgical instrument. The flexible tensioning element bears against the side of the aperture in tensioning plate 902, and as the tensioning plate 902 rotates upward, the point at which the tensioning element bears against the side of the aperature moves upward, and so a path of the flexible tensioning element is adjusted.

In some implementations, flexible tensioning elements are routed through the gimbal. In this regard the gimbal changes the path length as it rotates and so imparts an actuating tension to the desired tensioning element.

In some implementations, rather than being routed through the gimbal 910, flexible tensioning elements are connected to the gimbal 910. In this regard, proximal ends of the flexible tensioning elements are moved away from the distal end component when the gimbal 910 rotates, thereby increasing length of the path for the desired tensioning elements to actuate the distal end component.

Figure 9B:
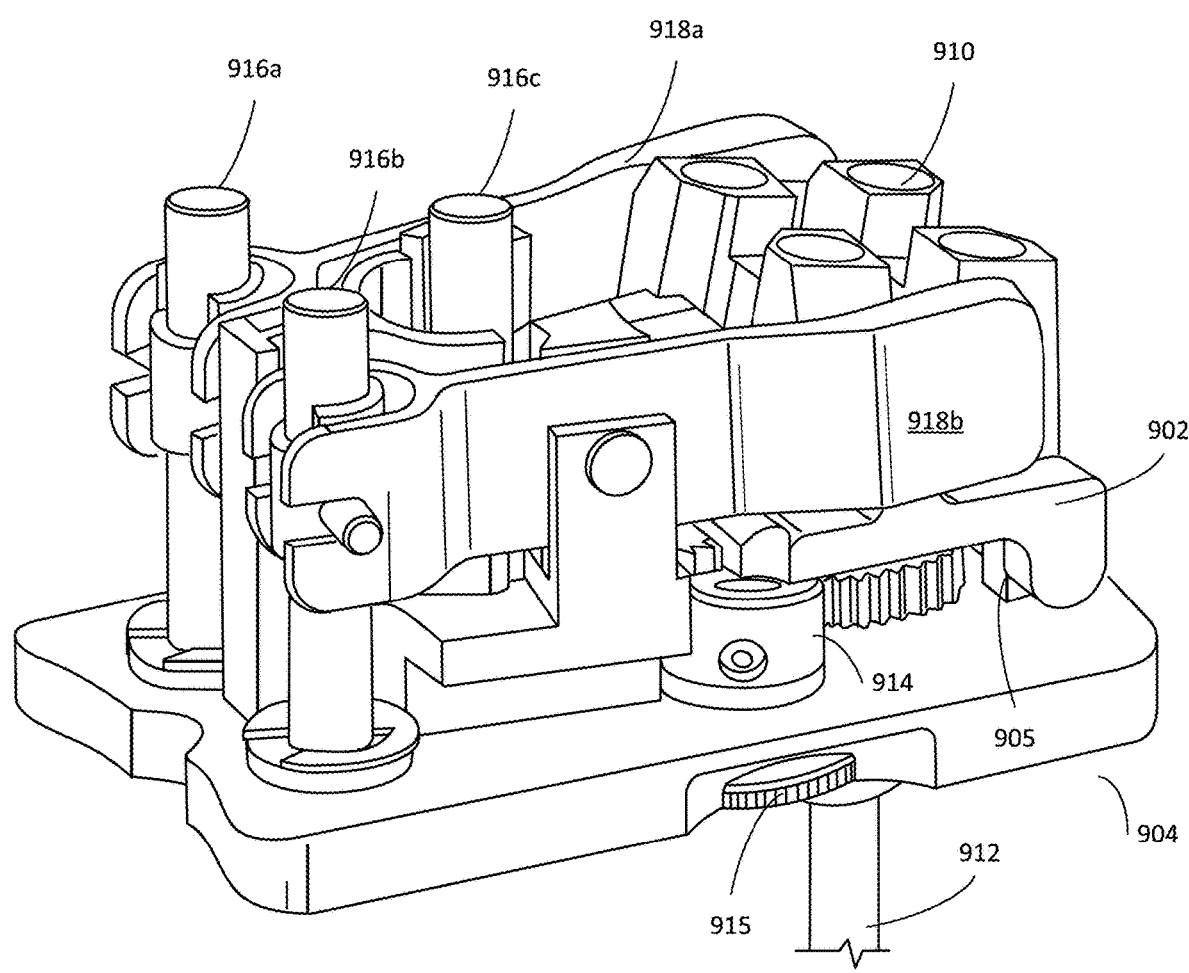
Figure 10:
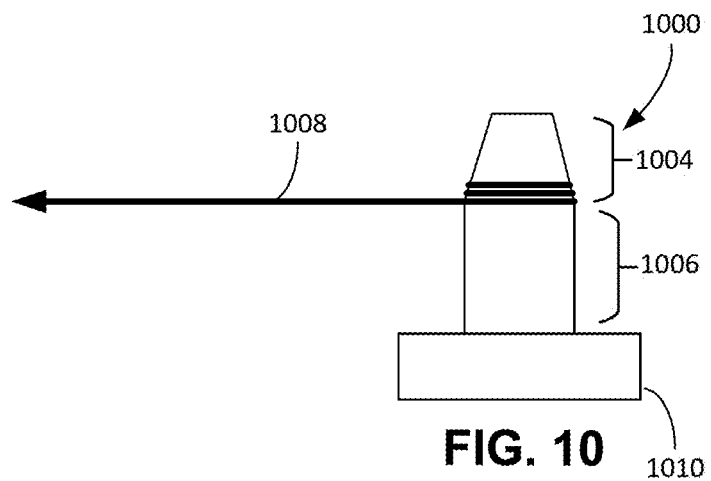
FIG. 10 is a side schematic view of an example of a dynamic tensioner.

Whether the flexible tensioning element are routed through the gimbal 910 or is connected to the gimbal 910, the dynamic preload tensioner 900 can be operated to adjust a path of the flexible tensioning element and adjust a preload tension on the tensioning element. To rotate the tensioning plate 902 around the pin 905, the dynamic tensioner 900 includes, for example, as shown in FIG. 9B, a rotatable member 914 that engages the tensioning plate 902. As the rotatable member 914 rotates, a ramp formed on rotatable member 914 engages the tensioning plate 902 such that the tensioning plate 902 pivots about the pin 905, and thereby lengthens the path of the flexible tensioning element. A drive component 915 of the surgical instrument, in some cases, is driven by the drive system of the manipulator to rotate the rotatable member 914.

In some implementations, to steer the distal end component, the drive system, e.g., of the manipulator, operates lead screws 916a, 916b, and 916c. The lead screws 916a, 916b, 916c, when operated, rotate arms 918a, 918b, 918c, respectively, such that the gimbal 910 pivots relative to the chassis 904. As the gimbal 910 pivots, the gimbal 910 bears against the flexible tensioning elements to adjust the paths of the flexible tensioning elements, thereby causing the flexible tensioning elements to experience tension. The multiple flexible tensioning elements are drivable by the lead screws 916a, 916b, 916c to move the distal end component in multiple degrees of freedom. Alternatively or additionally, the drive system drives a gear system 920 to roll the distal end component.

A number of implementations have been described. Nevertheless, it will be understood that various modifications may be made.

In some implementations, the preload tension applied to the flexible tensioning element is controlled during a surgical operation. For example, while the distal end component is being steered during the surgical operation by using a subset of the drive outputs of the drive system of the manipulator, another drive output is operable to adjust the preload tension applied to the flexible tensioning element without steering the distal end component. The surgical instrument includes, for example, of one of the dynamic preload tensioners described herein, and the preload tension is applied before the distal end component is steered for the surgical operation.

In some implementations, the preload tension is adjusted during a surgical operation as loads applied to the distal end component vary during the surgical operation. As the loads on the distal end component increase due to contact with patient tissue, for example, the preload tension is increased. In cases in which the loads on the distal end component are low, e.g., when the distal end component is being steered in space absent contact with patient tissue, the dynamically adjustable preload tension is decreased. In some implementations, the surgical instrument is a surgical stapler system, and the dynamically adjustable preload tension is increased when the stapler system is to be clamped.

In some implementations, the dynamic preload tensioner for a flexible tensioning element includes the drive component operated to steer the distal end component by using the flexible tensioning element. The flexible tensioning element is, for example, twisted to change a path of the flexible tensioning element. In the example shown in FIG. 10, a dynamic preload tensioner 1000 includes a first portion 1004 and a second portion 1006. The dynamic tensioner 1000 is, for example a rotatable capstan in which the first portion 1004 has a first diameter, and the second portion 1006 has a second diameter, the first diameter being smaller than the second diameter. At a distal end, the flexible tensioning element 1008 is attached to a distal end component. At a proximal end, the flexible tensioning element 1008 is attached to the dynamic tensioner 1000 such that it can be driven by the dynamic tensioner 1000 and such that it can be selectively wrapped around the different portions 1004, 1006. The dynamic tensioner 1000 includes a drive component 1010, e.g., the drive component 104a, that can be driven to apply tension to the flexible tensioning element 1008 to steer the distal end component to which the flexible tensioning element 1008 is coupled.

When the drive component 1010 is driven by, for example, the drive system of the manipulator, the dynamic tensioner 1000 is rotated. To steer the distal end component, the dynamic tensioner 1000 is rotated to apply tension to the flexible tensioning element 1008. To apply the adjustable preload tension to the flexible tensioning element 1008, the flexible tensioning element 1008 is wrapped around a selected portion of the capstan. When the flexible tensioning element 1008 is wrapped around the second portion 1006, a path of the flexible tensioning element 1008 is adjusted such that a preload tension is applied to the flexible tensioning element 1008. In some cases, in an initial state of the surgical instrument, the flexible tensioning element 1008 is wrapped around the first portion 1004. To add preload tension to the flexible tensioning element, the flexible tensioning element 1008 is wrapped around the second portion 1006. In some cases, to add preload tension to the flexible tensioning element 1008, the flexible tensioning element 1008 is moved from an initial state in which it is wrapped around the first portion 1004 to an operating state in which it is wrapped around both the first portion 1004 and the second portion 1006. In some implementations, if the flexible tensioning element 1008 is driven to move the distal end effector in a first direction along a degree of freedom and another flexible tensioning element is driven to move the distal end effector in a second direction along the degree of freedom, the other flexible tensioning element is attached to separate drive component and dynamic tensioner.

Figure 11A:
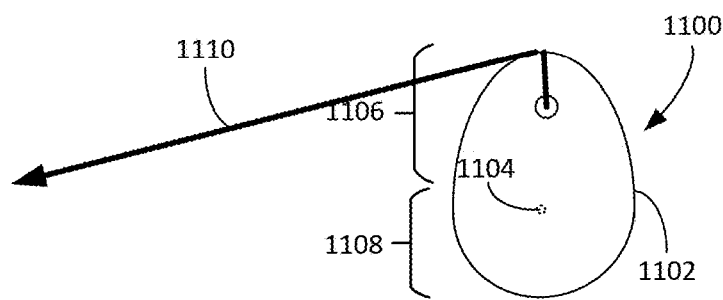
FIG. 11A is a top schematic view of a dynamic tensioner in a first position.
Figure 11B:
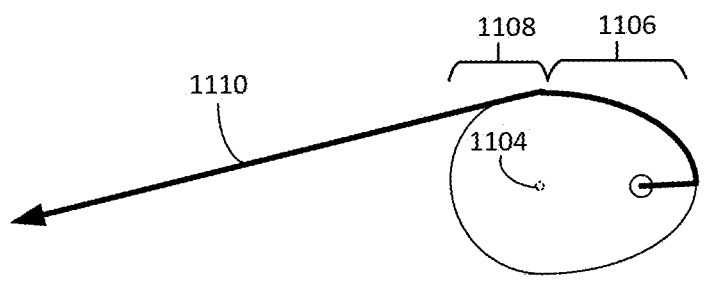
FIG. 11B is a top schematic view of the dynamic tensioner of FIG. 11A in a second position.

As shown in FIGS. 11A and 11B, in some implementations, rather than having multiple portions having different diameters, a dynamic preload tensioner 1100 includes a horizontal section 1102 having an oblong profile, an oval profile, and/or a non-circular profile. The dynamic tensioner 1100 is mounted to a chassis of the surgical instrument such that the dynamic tensioner 1100 is rotatable about a center of rotation 1104. A drive component (not shown) is drivable by a drive system of a surgical manipulator as described above to rotate the dynamic preload tensioner 1100. The horizontal section 1102 includes, for instance, a first zone 1106 and a second zone 1108. The first zone 1106 has a profile with a distance to the center of rotation 1104 that varies along its length. The second zone 1108, for instance, has a circular profile with constant distance between the profile and the center of rotation 1104 of the horizontal section 1102.

The flexible tensioning element 1110 is attached to the dynamic tensioner 1100 such that it wraps around the horizontal section 1102 of the capstan. To add preload tension to the flexible tensioning element 1110, the flexible tensioning element 1110 is wrapped around the first zone 1106. A path of the flexible tensioning element 1110 changes, e.g., a length of the path decreases, when the flexible tensioning element 1110 is wrapped around the first zone 1106. In an initial action, the flexible tensioning element 1110 is wrapped around the first zone 1106 to increase the preload tension from a first value to a second value. In an operating state in which preload tension has been added to the flexible tensioning element 1110, the flexible tensioning element 1110 is wrapped around both the first zone 1106 and the second zone 1108. The flexible tensioning element 1110 extends away from the dynamic tensioner 1100 beginning at the second zone 1108 such that the amount of length of the flexible tensioning element 1110 that is wound onto the dynamic tensioner 1100 is proportional to the amount of rotation of the dynamic tensioner 1100. In contrast, when the flexible tensioning element 1110 extends away from the dynamic tensioner 1100 beginning at the first zone, a greater amount of length of the flexible tensioning element is wound onto the dynamic tensioner 1100 given an amount of rotation of the dynamic tensioner 1100. The dynamic tensioner 1100 is rotated to drive the flexible tensioning element from the initial state to the operation state. In some implementations, if the flexible tensioning element 1110 is driven to move the distal end effector in a first direction along a degree of freedom and another flexible tensioning element is driven to move the distal end effector in a second direction along the degree of freedom, the other flexible tensioning element is attached to separate drive component and dynamic tensioner.

While the drive system of the manipulator has been described as operating the dynamic preload tensioner, in some implementations, a manually operable preload tensioning tool is operated, e.g., by a nurse, a clinician, or a surgeon, to operate the dynamic tensioner. The tensioning tool is, for example, a switch, a knob, or other device on an exterior surface of the chassis of the surgical instrument that the operator manually operates the dynamic tensioner to adjust the path of the flexible tensioning element. When operated, the tensioning tool is lockable in place such that the preload tension provided by the adjusted path of the flexible tensioning element is maintained. The tensioning tool is, in some cases, coupled to a mechanism for a dynamic tensioner described in the examples herein. The tensioning tool, for instance, is substituted for the drive component such that the preload tension is added through manual operation of the tensioning tool rather than through operation of an actuator coupled to the drive component.

In some implementations, the dynamic preload tensioner includes a pin movably mounted to the chassis and engageable with the flexible tensioning element to change the path of the flexible tensioning element when the pin is moved relative to the chassis. The pin, for instance, applies a transverse load on the flexible tensioning element that bends the flexible tensioning element at a location at which the pin contacts the flexible tensioning element. The bending of the flexible tensioning element changes a path of the flexible tensioning element, e.g., increases a path length. The path change thereby adds a preload tension to the flexible tensioning element.

The examples presented herein indicate that the dynamic tensioner, in some cases, is lockable such that the preload tension added using the dynamic tensioner can be maintained. In some implementations, the dynamic tensioner is lockable at one of several discrete positions. The dynamic tensioner, for instance, includes a ratcheting mechanism that adds preload tension to the flexible tensioning element as the ratcheting mechanism is advanced. In some cases, the ratcheting mechanism is resettable to reduce the preload tension on the flexible tensioning element.

In some implementations, the dynamic preload tensioner rotates the tubular member relative to the chassis. For instance, referring back to FIG. 1, an alternative dynamic tensioner causes the tubular member 115 to rotate relative to the chassis 102 about a point at which the tubular member 115 and the chassis 102 are connected. At the location at which the flexible tensioning element 106 enters the tubular member 115, the surgical instrument 101 includes, for example, a bearing surface that the flexible tensioning element 106 engages when the tubular member 115 is rotated relative to the chassis 102. The engagement between the bearing surface and the flexible tensioning element 106 changes the path of the flexible tensioning element 106, e.g., increases a path length.

In some implementations, the preload tension is added to the flexible tensioning element only when the surgical instrument is mounted to the manipulator. The controller, for example, only operates the drive system of the manipulator upon detecting that the surgical instrument has been mounted to the manipulator. In some cases, the driven interface assembly of the manipulator engages with actuation levers on the surgical instrument. The actuation levers, upon being actuated, activate the dynamic preload tensioner to add the preload tension to the flexible tensioning element. In some implementations, the driven interface assembly of the manipulator includes a sensor to detect engagement with the surgical instrument. Upon detecting engagement of the driven interface assembly of the manipulator with the surgical instrument, the sensor transmits a signal to the controller, which in turn operates the actuator to drive the drive component coupled to the dynamic tensioner.

While locking mechanisms and techniques have been described with respect to some implementations, in some cases, the controller of the manipulator operates the drive output to maintain the position of the dynamic tensioner and hence maintain the preload tension in the flexible tensioning element. In cases in which the dynamic tensioner is coupled to a drive component driven by a drive output of the manipulator, the controller locks the actuator to inhibit rotation of the drive component. The controller, for instance, locks the actuator in response to determining that the tension in the flexible tensioning element is above a predefined threshold.

Accordingly, other implementations are within the scope of the claims.

What is claimed is:

1. A surgical instrument comprising:
   a chassis at a proximal end;
   a distal end component at a distal end;
   a tubular member coupled to the chassis and extending from the chassis to the distal end component, the tubular member having a longitudinal axis;
   a drive component mounted in the chassis;
   a flexible tensioning element coupled to the drive component, extending through the tubular member, and coupled to the distal end component; and
   a dynamic preload tensioner engaged with the tubular member, the dynamic preload tensioner configured to move the tubular member in translation along the longitudinal axis of the tubular member and relative to the chassis to change a path of the flexible tensioning element.

2. The surgical instrument of claim 1, wherein:
   the dynamic preload tensioner is located on a proximal end of the tubular member.

3. The surgical instrument of claim 1, further comprising:
   a rotatable member through which the flexible tensioning element extends, the rotatable member configured to be rotated to cause rotation of the tubular member and the distal end component.

4. The surgical instrument of claim 3, wherein:
the rotatable member comprises a gear portion.

5. The surgical instrument of claim 3, wherein:
the rotatable member is a first rotatable member, and
the dynamic preload tensioner comprises a second rotatable member movable in translation along the longitudinal axis of the tubular member to cause the tubular member and the first rotatable member to move in translation along the longitudinal axis to change the path of the flexible tensioning element.

6. The surgical instrument of claim 5, wherein:
the second rotatable member is rotatable relative to a portion of the chassis, and
the second rotatable member is movable in translation along the longitudinal axis in response to rotating about relative to the portion of the chassis.

7. The surgical instrument of claim 6, wherein:
the first rotatable member is configured to engage with the second rotatable member at a predefined orientation such that the second rotatable member rotates relative to the portion of the chassis.

8. The surgical instrument of claim 6, wherein:
the second rotatable member is movable along a ramp formed on the portion of the chassis as the second rotatable member is rotated relative to the portion of the chassis.

9. The surgical instrument of claim 6, wherein:
the second rotatable member comprises a locking portion configured to engage a corresponding locking portion on the portion of the chassis to lock a position of the second rotatable member.

10. The surgical instrument of claim 5, wherein:
the second rotatable member is lockable to one of multiple discrete positions.

11. The surgical instrument of claim 5, wherein:
the first rotatable member is configured to contact the second rotatable member to cause the second rotatable member to move from a first axial position to a second axial position to change the path of the flexible tensioning element and is further configured to contact the second rotatable member to move the second rotatable member from the second axial position to the first axial position.

12. The surgical instrument of claim 5, wherein:
the first rotatable member is positioned distal to the second rotatable member, and
the tubular member is positioned distal to the second rotatable member.

13. The surgical instrument of claim 3, wherein:
the rotatable member is rotatable within a first predefined range and a second predefined range such that rotation of the rotatable member in the first predefined range causes rotation of the tubular member and the distal end component and such that rotation of the rotatable member in the second predefined range causes movement of the tubular member and the distal end component in translation along the longitudinal axis of the tubular member in a distal direction to change the path of the flexible tensioning element.

14. The surgical instrument of claim 1, wherein:
the flexible tensioning element extends through the dynamic preload tensioner.

15. The surgical instrument of claim 8, wherein:
the ramp follows a helical path.

16. The surgical instrument of claim 1, wherein:
the drive component is a first drive component,
the surgical instrument comprises a second drive component mounted in the chassis and configured to drive rotation of the tubular member and distal end component about the longitudinal axis of the tubular member, and
the dynamic preload tensioner is configured to be driven in rotation by the second drive component.

17. A method comprising:
causing a tubular member coupled to and extending from a chassis of a surgical instrument to move in translation along a longitudinal axis of the tubular member and relative to the chassis to adjust a preload tension in a flexible tensioning element of the surgical instrument, wherein the flexible tensioning element of the surgical instrument is coupled to a drive component mounted in the chassis of the surgical instrument, extends through the tubular member, and is coupled to a distal end component of the surgical instrument coupled to a distal end of the tubular member; and
causing the distal end component of the surgical instrument to move using the drive component and the flexible tensioning element.

18. The method of claim 17, wherein:
causing the tubular member to move comprises:
causing a dynamic preload tensioner coupled to a proximal end portion of the tubular member to move in translation relative to the chassis of the surgical instrument.

19. The method of claim 17, wherein causing the distal end component of the surgical instrument to move using the drive component and the flexible tensioning element comprises causing the distal end component to move while maintaining a position of the tubular member.

* * * * *

UNITED STATES PATENT AND TRADEMARK OFFICE
CERTIFICATE OF CORRECTION

| | | |
|---|---|---|
| PATENT NO. | : 12,426,974 B2 | Page 1 of 1 |
| APPLICATION NO. | : 17/488881 | |
| DATED | : September 30, 2025 | |
| INVENTOR(S) | : Matthew Aaron Wixey et al. | |

It is certified that error appears in the above-identified patent and that said Letters Patent is hereby corrected as shown below:

In the Claims

In Claim 6, at Column 27, Line 15, delete "about".

Signed and Sealed this
Sixteenth Day of December, 2025

John A. Squires
*Director of the United States Patent and Trademark Office*